(12) United States Patent
Fishberger et al.

(10) Patent No.: US 9,986,965 B2
(45) Date of Patent: Jun. 5, 2018

(54) STETHOSCOPE COVERS AND DISPENSING SYSTEM FOR STETHOSCOPE COVERS

(71) Applicants: Kenneth Irwin Fishberger, Setauket, NY (US); Ross Fishberger, Seatauket, NY (US)

(72) Inventors: Kenneth Irwin Fishberger, Setauket, NY (US); Ross Fishberger, Seatauket, NY (US)

( * ) Notice: Subject to any disclaimer, the term of this patent is extended or adjusted under 35 U.S.C. 154(b) by 0 days. days.

(21) Appl. No.: 15/067,988

(22) Filed: Mar. 11, 2016

(65) Prior Publication Data

US 2017/0258435 A1    Sep. 14, 2017

(51) Int. Cl.
*A61B 7/02* (2006.01)
*B65H 16/00* (2006.01)
*B65H 18/10* (2006.01)

(52) U.S. Cl.
CPC ............ *A61B 7/02* (2013.01); *B65H 16/005* (2013.01); *B65H 18/103* (2013.01); *B65H 2403/47* (2013.01)

(58) Field of Classification Search
CPC .................................................... B65H 16/00
See application file for complete search history.

(56) References Cited

U.S. PATENT DOCUMENTS

| | | | |
|---|---|---|---|
| 2,824,774 A | 2/1958 | Embree | |
| 4,669,678 A * | 6/1987 | Navarro | B65H 23/1955 242/413.6 |
| 4,846,412 A | 7/1989 | Morand | |
| 5,065,894 A * | 11/1991 | Garland | A61F 15/002 221/25 |
| 5,065,896 A * | 11/1991 | Jurgich | B65C 9/0006 156/465 |
| 5,145,299 A * | 9/1992 | Stephenson, Jr. | B60P 7/083 24/265 CD |
| 5,808,244 A * | 9/1998 | Knight | A61B 7/02 181/131 |
| 5,863,384 A * | 1/1999 | Reddy | B65C 11/00 156/576 |
| 5,975,083 A * | 11/1999 | Henderson, Jr. | A41D 13/082 128/878 |
| 6,206,134 B1 * | 3/2001 | Stark | A61B 46/10 181/131 |
| 7,117,971 B1 | 10/2006 | Cornacchia | |

(Continued)

FOREIGN PATENT DOCUMENTS

KR    101109039 B1    2/2012

OTHER PUBLICATIONS

Extended European Search Report, dated Dec. 3, 2018, European Patent Application No. 17 189132.8.

*Primary Examiner* — Gene O Crawford
*Assistant Examiner* — Ayodeji T Ojofeitimi
(74) *Attorney, Agent, or Firm* — Sorell Lenna & Schmidt, LLP

(57) ABSTRACT

A dispensing system is provided including a housing having a cavity, a first opening and a second opening, the openings being in communication with the cavity. First and second rollers are positioned within the cavity. A strip extends through the openings. The strip has a first end that is wound about the first roller and a second end that is wound about the second roller. A plurality of instrument covers are removably positioned on the strip. Methods of use and kits are disclosed.

20 Claims, 22 Drawing Sheets

(56) References Cited

U.S. PATENT DOCUMENTS

| | | | |
|---|---|---|---|
| 7,614,477 B2 * | 11/2009 | Statner | A61B 46/10 181/131 |
| 8,662,244 B2 | 3/2014 | Fishberger et al. | |
| 2011/0186590 A1 | 8/2011 | Lee | |
| 2015/0128997 A1 | 5/2015 | Lesic | |

* cited by examiner

STETHOSCOPE COVERS AND DISPENSING SYSTEM FOR STETHOSCOPE COVERS

TECHNICAL FIELD

The present disclosure generally relates to medical devices, and more particularly to instrument covers and a dispensing system that stores and dispenses instrument covers for medical devices such as, for example, stethoscopes. Methods of use and kits are also disclosed.

BACKGROUND

A stethoscope is an acoustic medical device typically used by a physician or medical care provider to monitor sounds in a patient's organs and/or pathways (respiratory, cardiac, arterial, etc.). Stethoscopes typically include a chest piece for placement against the patient for sensing relatively high frequency sound, an air-filled hollow tube to transmit the sound from the chest piece, and ear tubes to receive the sound from the air-filled hollow tube and transmit the sound via ear tips to the physician or medical care provider. The chest piece is generally known to include a head and a diaphragm, which is the part of the chest piece placed against the patient. When the diaphragm is placed on the patient, bodily sounds vibrate the diaphragm creating acoustic pressure sound waves which travel up the air-filled hollow tube and ear tubes to the physician or medical care provider's ears. The physician or medical care provider may then be better able to diagnose a condition or whether the patient's organs or pathways are functioning normally.

In use, the head and diaphragm of a stethoscope can easily be contaminated with bacteria and other contaminants as stethoscopes are typically used on several different patients every hour, the patients being affected by different contaminants. Physicians or medical care providers in a hospital setting see about 20-30 patients an hour including neonatal and pediatric patients, surgery patients, cancer and infectious disease patients and often examine these patients using the same stethoscope. Medical providers typically employ a stethoscope on most of the patients they see in a hospital setting and anywhere between 6-12 patients per hour in an office setting. Transmission of bacterial infections among patients, particularly in a hospital setting, is of great concern especially in view of the development of antibiotic-resistant strains of staphylococcal infections and other resistant strains of bacteria, viruses, and fungal infections. Examples of resistant strains of bacteria include but are limited to, vancomycin resistant *enterococcus* and *clostridium* dificile; viruses such as hepatitis B and C; and fungal infections such as aspergillosis *candida*.

Conventional stethoscope covers include a thin sheet of plastic having an adhesive backing which can be applied over the diaphragm of a stethoscope before use on each new patient. After use, the cover is typically removed and discarded. These covers can function adequately; however, problems arise with the use of such covers. Such problems include the cover falling off the stethoscope during application, the cover not fitting with an air-tight seal on the diaphragm during application, poor acoustic transmission and the transmission of microorganisms, fluids or other contaminants to the head of the stethoscope and in some cases, the diaphragm of the stethoscope. Additionally, dispensers for such covers are often cumbersome and/or make it difficult to dispense the covers. This disclosure describes an improvement over these prior art technologies.

SUMMARY

In some embodiments, a dispensing system is provided that includes a housing having a cavity, a first opening and a second opening. The openings are in communication with the cavity. First and second rollers are positioned within the cavity. A strip extends through the openings. The strip has a first end that is wound about the first roller and a second end that is wound about the second roller. A plurality of instrument covers are removably positioned on the strip. Methods of use and kits are disclosed.

In some embodiments, the instrument covers define an elongated segment, such as, for example a layer or band that extends the entire length of the strip. In some embodiments, the instrument covers are separated from one another by a series of perforations. In some embodiments, the instrument covers are spaced apart from one another on the strip. In some embodiments, the instrument covers are acoustically transmissive and substantially impermeable to microorganisms and fluids. In some embodiments, the instrument covers each comprise a first surface and an opposite second surface having non-stick properties that prevent the second surface from permanently adhering to a strip. In some embodiments, the second surface prevents the instrument covers from permanently adhering to the strip such that the instrument covers can be easily removed from the strip. In some embodiments, static cling from the second surface and/or the strip removably couples the instrument covers to the strip. In some embodiments, the first surface comprises a material having adhesion properties. In some embodiments, the first surface is configured to be removably attached to the head of a stethoscope such that the instrument cover will not fall off the stethoscope during use by a physician or medical provider. In some embodiments, the first surface is made of a material having adhesion properties. In some embodiments, the first surface is coated with a material having adhesion properties. In some embodiments, the strip is provided in a roll such that the second surfaces of the instrument covers contact one another to maintain the strip and the instrument covers in a roll.

In some embodiments, each of the instrument covers is sized and configured to removably cover the diaphragm and the head of a stethoscope simultaneously by form-fitting a respective first surface with outer surfaces of the diaphragm and the head. In some embodiments, the instrument covers are made from one or more of polyvinyl chloride, polyvinylidene chloride, low density polyethylene, linear low density polyethylene, polyisobutene, poly[ethylene-vinylacetate] copolymer and lightweight aluminum foil. In some embodiments, the instrument covers are made from one or more of a cellophane, vinyl, acetate, polyethylene acrylic, butyl rubber, ethylene-vinyl acetate, natural rubber, a nitrile, silicone rubber, a styrene block copolymer, a vinyl ether and a tackifier. In some embodiments, the instrument covers each include an antimicrobial substance that can neutralize or destroy microbes. In some embodiments, the material(s) that form(s) the instrument covers comprises the antimicrobial substance. That is, the antimicrobial substance is distributed throughout a thickness of each of the instrument covers and/or on the first and/or second surfaces of the instrument covers. In some embodiments, at least one of the first and second surfaces is coated with the antimicrobial substance.

In some embodiments, the housing comprises an antimicrobial material. In some embodiments, the housing is configured for mounting on a vertical surface, such as, for example, a wall or a horizontal surface, such as, for example, a table. In some embodiments, an antimicrobial ultraviolet light source is positioned within the cavity of the housing. In some embodiments, the housing is disposable and may be made from materials, such as, for example, cardboard. In some embodiments, the housing is reusable and may be made from materials, such as, for example, plastic.

In one embodiment, in accordance with the principles of the present disclosure, a method for dispensing instrument covers is provided. The method comprises rotating a second roller relative to a housing to advance a strip having instrument covers removably positioned on the strip such that one of the instrument covers is positioned between first and second openings of the housing and the strip engages an outer surface of the housing. In some embodiments, rotating the second roller causes the strip to unwind from a first roller that is positioned within the housing. In some embodiments, the method further comprises contacting the instrument cover that is positioned between first and second openings of the housing with a portion of a stethoscope, such as, for example, a head of a stethoscope, and positioning the instrument cover that is positioned between first and second openings of the housing about the head. In some embodiments, positioning the instrument cover comprises crimping the instrument cover about the head and/or at least a portion of a hollow tube of the stethoscope that is coupled to the head of the stethoscope. In some embodiments, the method includes rotating the second roller relative to the housing to advance the strip such that another one of the instrument covers is positioned between first and second openings of the housing.

In one embodiment, in accordance with the principles of the present disclosure, a kit is provided. The kit comprises a dispensing system comprising: a housing comprising a cavity, a first opening and a second opening, the openings being in communication with the cavity, a first roller positioned within the cavity, a second roller positioned within the cavity, a strip extending through the openings, the strip having a first end that is wound about the first roller and a second end that is wound about the second roller, and a plurality of instrument covers positioned on one side of the strip. The kit further includes at least one box of gloves and at least one stethoscope.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
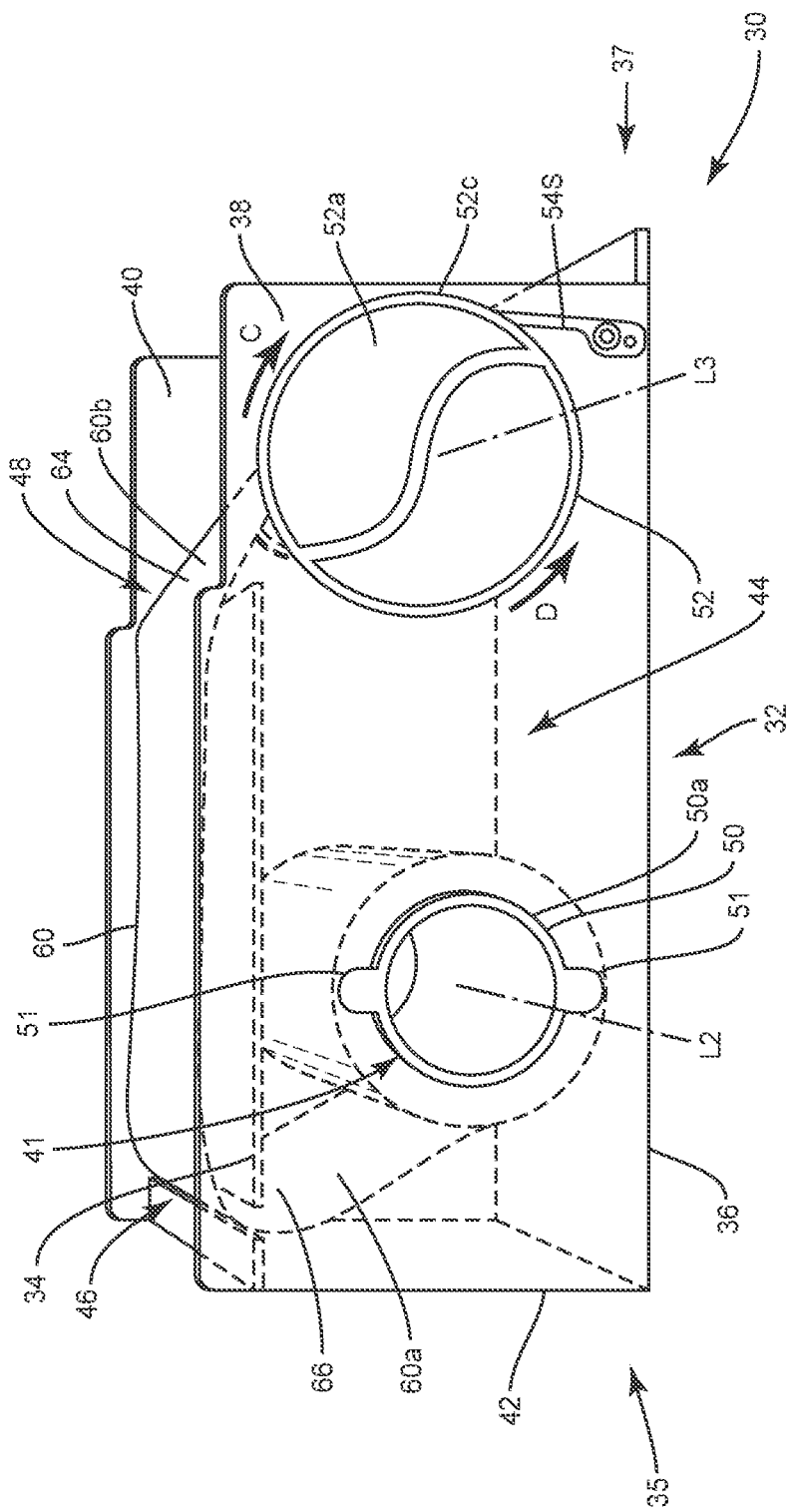
FIG. 1 is a side view of one embodiment of a dispensing system in accordance with the principles of the present disclosure.
Figure 2:
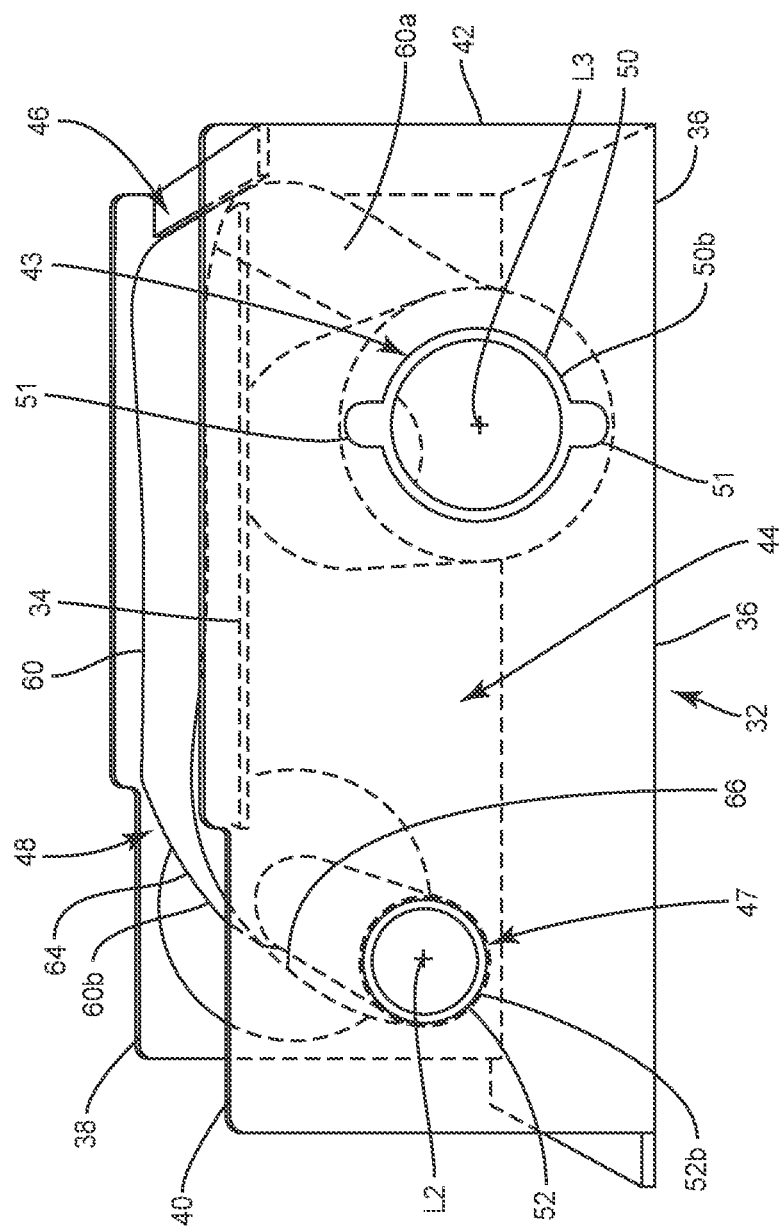
FIG. 2 is a side view of the dispensing system shown in FIG. 1.

The exemplary embodiments of the dispensing system and related methods of use disclosed are discussed in terms of medical devices, and more particularly to a dispensing system that stores and dispenses covers for medical devices. It is envisioned that the dispensing system may be employed in a hospital setting or a medical practitioner's examination room or office. The dispensing system includes a housing configured to hold and dispense acoustically transmissive instrument covers. In some embodiments, the instrument covers are each configured to securely fit onto the head and/or diaphragm of a medical instrument, such as, for example, a stethoscope such that the instrument cover forms an air-tight seal without any air bubbles or wrinkling of the instrument cover to prevent cross-contamination from patient to patient.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

The following disclosure includes a description of a dispensing system for holding and dispensing instrument covers. The disclosure also includes a description of related methods of employing the disclosed dispensing system and a description of a kit that includes the disclosed dispensing system. Alternate embodiments are also disclosed. Reference will now be made in detail to the exemplary embodiments of the present disclosure, which are illustrated in the accompanying figures. Turning now to FIGS. 1-22, there are illustrated components of a dispensing system, such as, for example, a dispensing system 30 and embodiments in accordance with the principles of the present disclosure.

The components of system 30 can be fabricated from biologically acceptable materials suitable for medical applications, depending on the particular application and/or preference of a medical practitioner. For example, the components of system 30, individually or collectively, can be fabricated from materials such as cellophane, vinyl, acetate, polyethylene acrylic, butyl rubber, ethylene-vinyl acetate, natural rubber, a nitrile, silicone rubber, a styrene block copolymer, a vinyl ether, a tackifier, antimicrobial and/or antiseptic materials including but are not limited to: alcohols such as ethanol, 1-propanol and 2-propanol/isopropanol or mixtures of these alcohols; sodium bicarbonate; hydrogen peroxide; benzalkonium chloride; chlorohexidine; hexachlorophene; iodine compounds; and combinations thereof. Antimicrobial materials that can be used include but are not limited to: beta-lactam antibiotics (such as penicillin, cephalosporin); protein synthesis inhibitors (such as amino-glycosides, macrolides, tetracycline, chloramphenicol, polypeptides); sulphonamides; cotrimoxazole; quinolones; antiviral agents; anti-fungal agents; anti-cancer drugs; anti-malarial drugs; anti-tuberculosis drugs; anti-leprotic drugs; anti-protozoal drugs and combinations thereof. In some embodiments, the components of system 30, individually or collectively, can be fabricated from materials such as polyvinyl chloride, polyvinylidene chloride, low density polyethylene, linear low density polyethylene, polyisobutene, poly[ethylene-vinylacetate] copolymer, lightweight aluminum foil and combinations thereof. In some embodiments, the components of system 30, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 30 may have material composites, including the above materials, to achieve various desired characteristics such as strength, rigidity, elasticity, compliance, biomechanical performance, durability and radiolucency or imaging preference. It is envisioned that the components of system 30 may be comprise antimicrobial and/or antiseptic materials. The components of system 30, individually or collectively, may also be fabricated from a heterogeneous material such as a combination of two or more of the above-described materials. The components of system 30 may be monolithically formed or integrally connected.

System 30 includes a housing 32 comprising opposite top and bottom walls 34, 36 and opposite first and second sidewalls 38, 40 that each extend between top and bottom walls 34, 36. That is, sidewalls 38, 40 each extend from top wall 34 to bottom wall 36. Housing 32 extends along a longitudinal axis L1 between a first end 35 and an opposite second end 37. In some embodiments, first end 35 comprises a rear wall 42 that extends between top and bottom walls 34, 36 and between first and second sidewalls 38, 40. That is, rear wall 42 extends from top wall 34 to bottom wall 36 and from first sidewall 38 to second sidewall 40. Inner surfaces of top and bottom walls 34, 36, first and second sidewalls 38, 40 and rear wall 42 define a cavity 44 of housing 32. Housing 32 comprises first and second openings 46, 48 that each extend through top wall 34. First and second openings 46, 48 are spaced apart from one another. First and second openings 46, 48 are each in communication with cavity 44.

In some embodiments, top and bottom walls 34, 36 extend parallel to one another. In some embodiments, top wall 34 extends transverse to bottom wall 36. In some embodiments, first and second sidewalls 38, 40 extend parallel to one another. In some embodiments, top and bottom walls 34, 36 and first and second sidewalls 38, 40 each extend parallel to longitudinal axis L1 and rear wall 42 extends perpendicular to longitudinal axis. In some embodiments, at least one of walls 34, 36, 48, 40, 42 may be disposed at alternate orientations, relative to longitudinal axis L1, such as, for example, transverse, perpendicular and/or other angular orientations such as acute or obtuse and/or may be offset or staggered.

In some embodiments, at least one of walls 34, 36, 48, 40, 42 comprises an antimicrobial material, such as, for example, a silver-based antimicrobial material, a copper-based antimicrobial material, chlorhexidene gluconate, benzalkonium chloride, a monoquaternary and/or polyquaternary ammonium salt-based antimicrobial material, a biguanide-based antimicrobial such as polyhexamethylene biguanide, triclosan, zinc pyrithione, an isothiazolinonebased antimicrobial, a 10,10'-oxybisphenoxarsine-based antimicrobial, a peptide-based antimicrobial, a natural antimicrobial such as hops extract, honey, a chitosan-based antimicrobial, and combinations thereof. In some embodiments, housing 32 is configured for mounting on a vertical surface such as, for example, a wall of a room, or a horizontal surface, such as, for example, a top surface of a desk or bench. In some embodiments, system 30 includes a bracket that is positioned on the vertical surface and/or the horizontal surface. In some embodiments, housing 32 is coupled the bracket and the bracket is positioned on the vertical surface and/or horizontal surface. In some embodiments, the bracket is mounted to the vertical surface and/or horizontal surface to fix the bracket to the vertical surface and/or horizontal surface. In some embodiments, housing 32 is disposable and comprises a material, such as, for example, cardboard.

Spaced apart first and second rollers 50, 52 are positioned in cavity 44. First roller 50 is positioned between rear wall 42 and second roller 52. First roller 50 is fixed relative to housing 32 and second roller 52 is rotatable relative to housing 32. That is, first roller 50 is prevented from rotating relative to housing 32. First roller extends along a longitudinal axis L2 and second roller extends along a longitudinal axis L3. Second roller 52 is rotatable relative to housing 32 about longitudinal axis L3 in opposite first and second directions, such as, for example, clockwise and counterclockwise. Longitudinal axes L2, L3 each extend transverse to longitudinal axis L1. In some embodiments, longitudinal axis L2 extends parallel to longitudinal axis L3. In some embodiments, longitudinal axes L2, L3 each extend perpendicular to longitudinal axis L1. In some embodiments, first and second rollers 50, 52 each have a tubular configuration. In some embodiments, first and second rollers 50, 52 are both hollow. In some embodiments, first roller 50 has a diameter that is greater than that of second roller 52. In some embodiments, second roller 52 has a diameter that is greater than that of first roller 50. In some embodiments, first and second rollers 50, 52 are each positioned equidistantly between top and bottom walls 34, 36. In some embodiments, first roller 50 and/or second roller 52 may have various cross section configurations, such as, for example, circular, oval, oblong, triangular, rectangular, square, polygonal, irregular, uniform, non-uniform, variable, tubular and/or tapered.

First roller 50 extends along longitudinal axis L2 between a first end 50a and an opposite second end 50b and second roller 52 extends along longitudinal axis L3 between a first end 52a and an opposite second end 52b. In some embodiments, first and second ends 50a, 50b, 52a, 52b of first and second rollers 50, 52 each extend through openings in first and second sidewalls 38, 40. In some embodiments, first end 50a of first roller 50 extends through an opening 41 that extends through the inner surface of first sidewalls 38 and an opposite outer surface of first sidewall 38 and second end 50b of first roller 50 extends through an opening 43 that extends through the inner and outer surfaces of second sidewall 40. In some embodiments, first end 52a of second roller 52 extends through an opening 45 that extends through the inner and outer surfaces of first sidewalls 38 and second end 52b of first roller 50 extends through an opening 47 that extends through the inner and outer surfaces of second sidewall 40. In some embodiments, first end 52a of second roller 52 is positioned outside of cavity 44 and defines a gripping portion 52c configured to be gripped and rotated by a hand of a physician or medical provider. In some embodiments, gripping portion 53c is positioned on second end 52b of second roller 52 and extends outside of cavity 44. In some embodiments, first and second ends 52a, 52b of second roller 52 each comprise a gripping portion 53c that is positioned outside of cavity 44.

Figure 4:
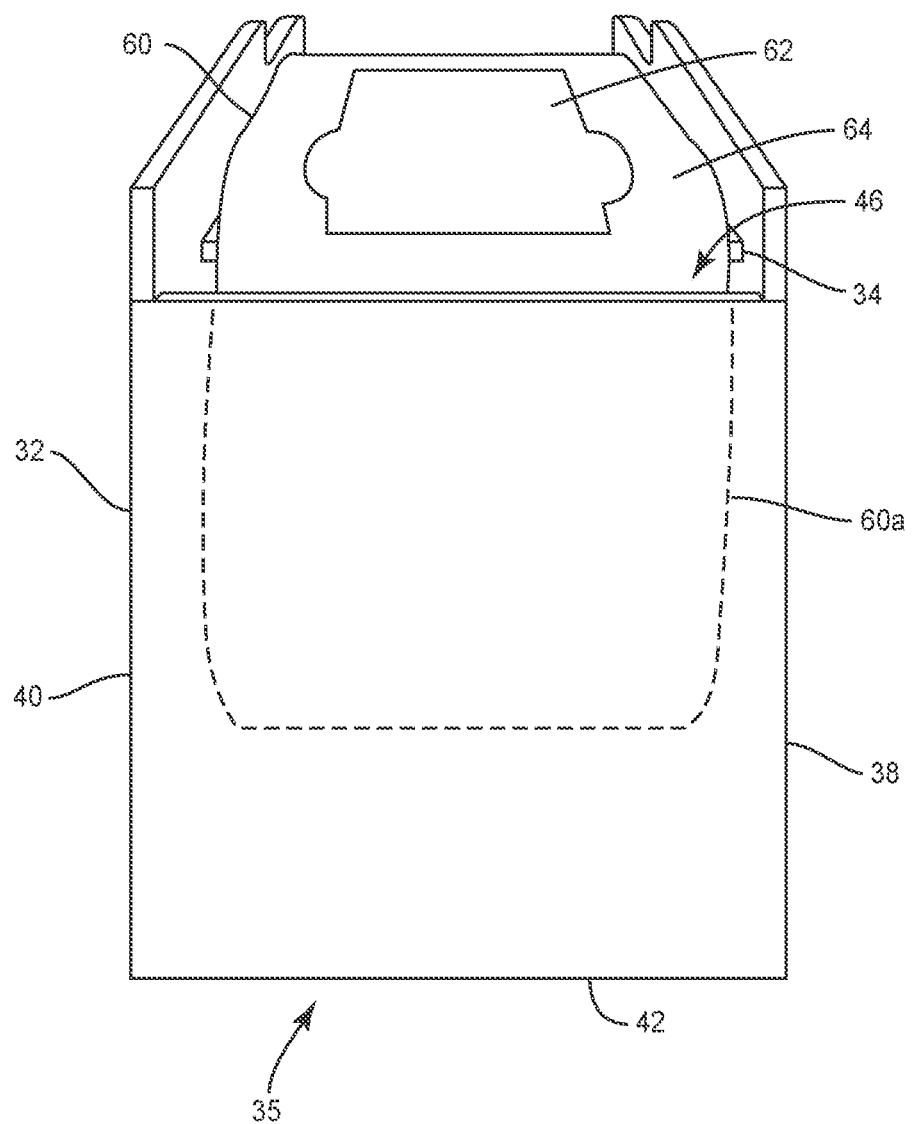
FIG. 4 is a rear view of the dispensing system shown in FIG. 1.
Figure 4A:
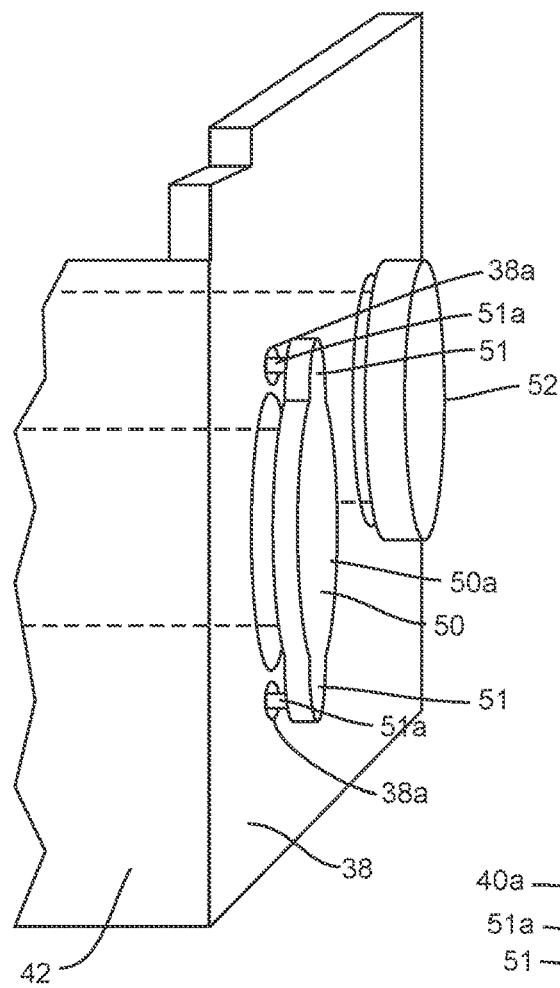
FIG. 4A is a close-up, perspective, rear view of the dispensing system shown in FIG. 1.
Figure 4B:
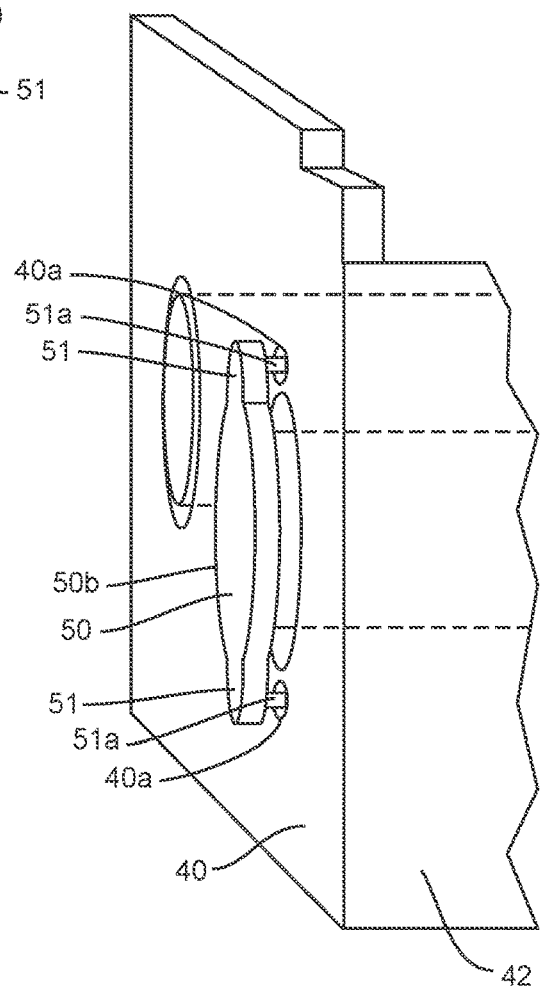
FIG. 4B is a close-up, perspective, rear view of the dispensing system shown in FIG. 1.

In some embodiments, first and second ends 50a, 50b of first roller 50 each comprise one or a plurality of tabs 51 that extend outwardly from a cylindrical portion of first roller 50. Tabs 51 are configured to prevent first roller 50 from rotating relative to housing 32. As shown in FIGS. 4A and 4B, tabs 51 each include a projection 51a that extends inwardly toward cavity 44. Projections 51a on tabs 51 on first end 50a of first roller 50 each extend into an opening 38a in first sidewall 38 to fix first end 50a to first sidewall 38 in a manner that prevents first end 50a from rotating relative to housing 32. Projections 51a on tabs 51 on second end 50b of first roller 50 each extend into an opening 40a in second sidewall 40 to fix second end 50b to second sidewall 40 in a manner that prevents second end 50b from rotating relative to housing 32. In some embodiments, projections 51a on tabs 51 on first end 50a of first roller 50 extend through first sidewall 38 such that projections 51a on tabs 51 on first end 50a are in communication with cavity 44. In some embodiments, projections 51a on tabs 51 on second end 50b of first roller 50 extend through second sidewall 40 such that projections 51a on tabs 51 on second end 50b are in communication with cavity 44. In some embodiments, openings 38a, 40a and/or projections 51a may have various cross section configurations, such as, for example, oval, oblong, triangular, rectangular, square, polygonal, irregular, uniform, non-uniform, variable, tubular and/or tapered. In some embodiments, first roller 50 is made up from two pieces that are separable to facilitate the insertion of projections 51a into openings 38a, 40a. That is, first end 50a of first roller 50 is separable from second end 50b of first roller. In some embodiments, first end 50a of first roller 50 is positioned within a cavity of second end 50b of first roller 50. In some embodiments, second end 50b of first roller 50 is positioned within a cavity of first end 50a of first roller 50.

In some embodiments, second roller 52 comprises a ratchet portion 52d positioned between gripping portion 52c and a cylindrical portion of second end 52b of second roller 52 and housing 32 comprises a part, such as, for example, a pawl 54 that is configured to engage ratchet portion 52d to permit second roller 52 to rotate relative to housing 32 about longitudinal axis L3 in a first direction, such as, for example, clockwise, and prevent second roller 52 from rotating relative to housing 32 about longitudinal axis L3 in an opposite second direction, such as, for example, counterclockwise. These features are shown in FIGS. 6-9, for example. In some embodiments, ratchet portion 52d comprises a plurality of teeth 56 that are configured to engage a projection 54a of pawl 54. Ratchet portion 52d comprises gaps 58 between adjacent teeth 56. In some embodiments, pawl 54 is deflectable relative to housing 32 as second roller 52 is rotated about longitudinal axis L3. In some embodiments, pawl 54 is deflectable relative to housing 32 in a first direction A, shown in FIG. 9, to allow projection 54a to incrementally move from one of gaps 58 to another one of gaps 58 as second roller 52 is rotated relative to housing 32 about longitudinal axis L3 in one direction, such as, for example clockwise. Projection 54a is biased relative to housing 32 in an opposite second direction B, shown in FIG. 9, to prevent second roller 52 from being rotated relative to housing 32 about longitudinal axis L3 in another direction, such as, for example, counterclockwise.

In some embodiments, teeth 56 are angled such that ratchet portion 52d and pawl 54 define a ratchet that allows second roller 52 to be incrementally rotated relative to housing 32 about longitudinal axis L3 in one direction, such as, for example, direction C in FIG. 1, yet prevents second roller 52 from being rotated relative to housing 32 about longitudinal axis L3 in another direction, such as, for example, direction D in FIG. 1. In particular, as second roller 52 is rotated relative to housing 32 about longitudinal axis L3 in direction D, projection 54a moves into one of gaps 58. Since pawl 54 is biased in direction B and teeth 56 are angled in the manner shown in FIGS. 6-8, further rotation of second roller 52 relative to housing 32 about longitudinal axis L3 in direction D is prevented. As second roller 52 is rotated relative to housing 32 about longitudinal axis L3 in direction C a first amount, projection 54a moves out of one of gaps 58 and slides along one of teeth 56. Further rotation of second roller 52 relative to housing 32 about longitudinal axis L3 in direction C causes projection 54a to move into one of gaps 58, since pawl 54 is biased relative to housing 32 in direction B. Second roller 52 may be further rotated relative to housing 32 about longitudinal axis L3 in direction C to move projection 54a such that projection 54a slides along teeth 58 to move projection 54a in and out of gaps 58 to incrementally rotate second roller 52 relative to housing 32 about longitudinal axis L3. This configuration allows second roller 52 to be selectively rotated relative to housing 32 about longitudinal axis L3 in direction C in any amount desired by a physician or medical care provider, as described herein.

Figure 7:
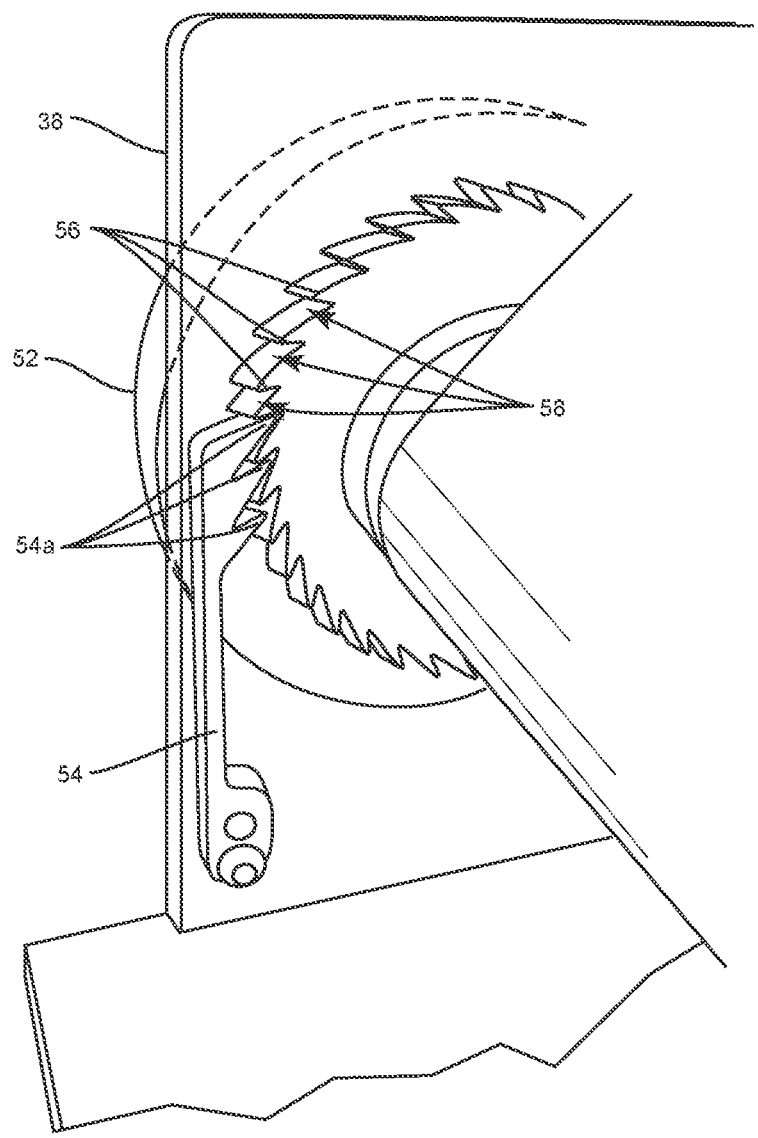
FIG. 7 is a close-up, perspective view of components of the dispensing system shown in FIG. 1.
Figure 8:
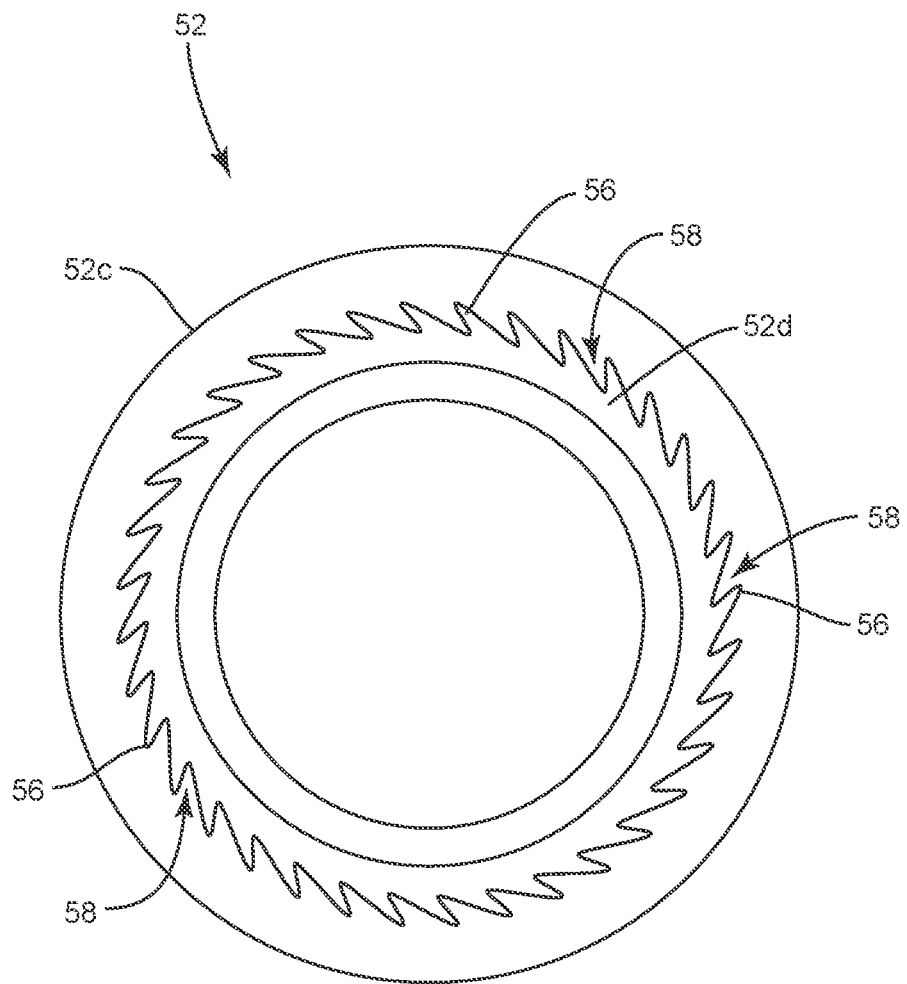
FIG. 8 is an end view of a component of the dispensing system shown in FIG. 1.
Figure 9:
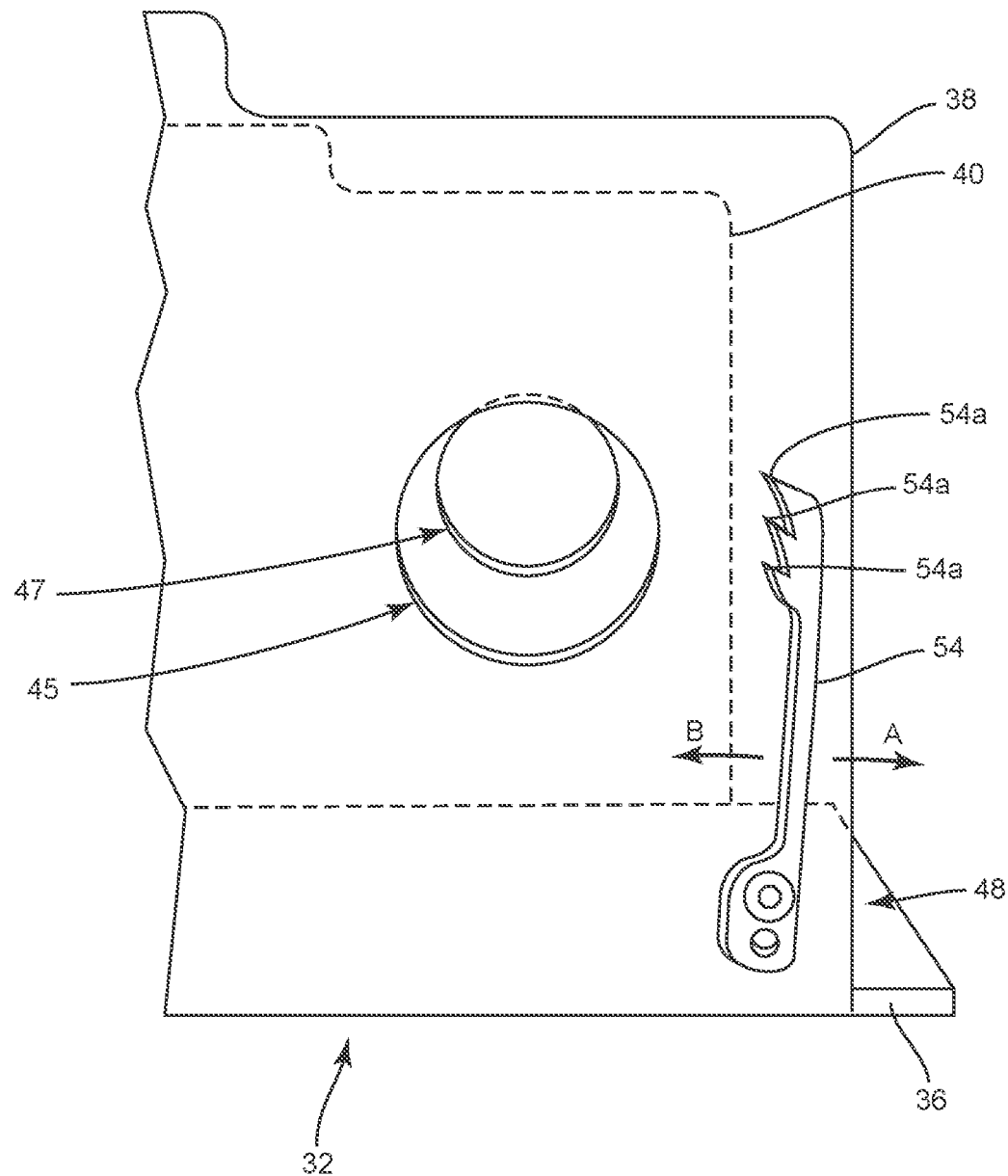
FIG. 9 is a side view of components of the dispensing system shown in FIG. 1.

In some embodiments, directions A and B and the angle of teeth 56 may be reversed such that the ratchet defined by ratchet portion 52 and pawl 54 allows second roller 52 to rotate relative to housing 32 about longitudinal axis L3 in direction D and prevents second roller 52 from rotating relative to housing 32 about longitudinal axis L3 in direction C. In some embodiments, projection 54a includes a plurality of projections 54a, as shown in FIGS. 7 and 9. In embodiments where projection 54a includes a plurality of projections 54a, each of projections 54a are configured for sliding along teeth 56 and disposal in one of gaps 58 in the manner discussed above.

Figure 5:
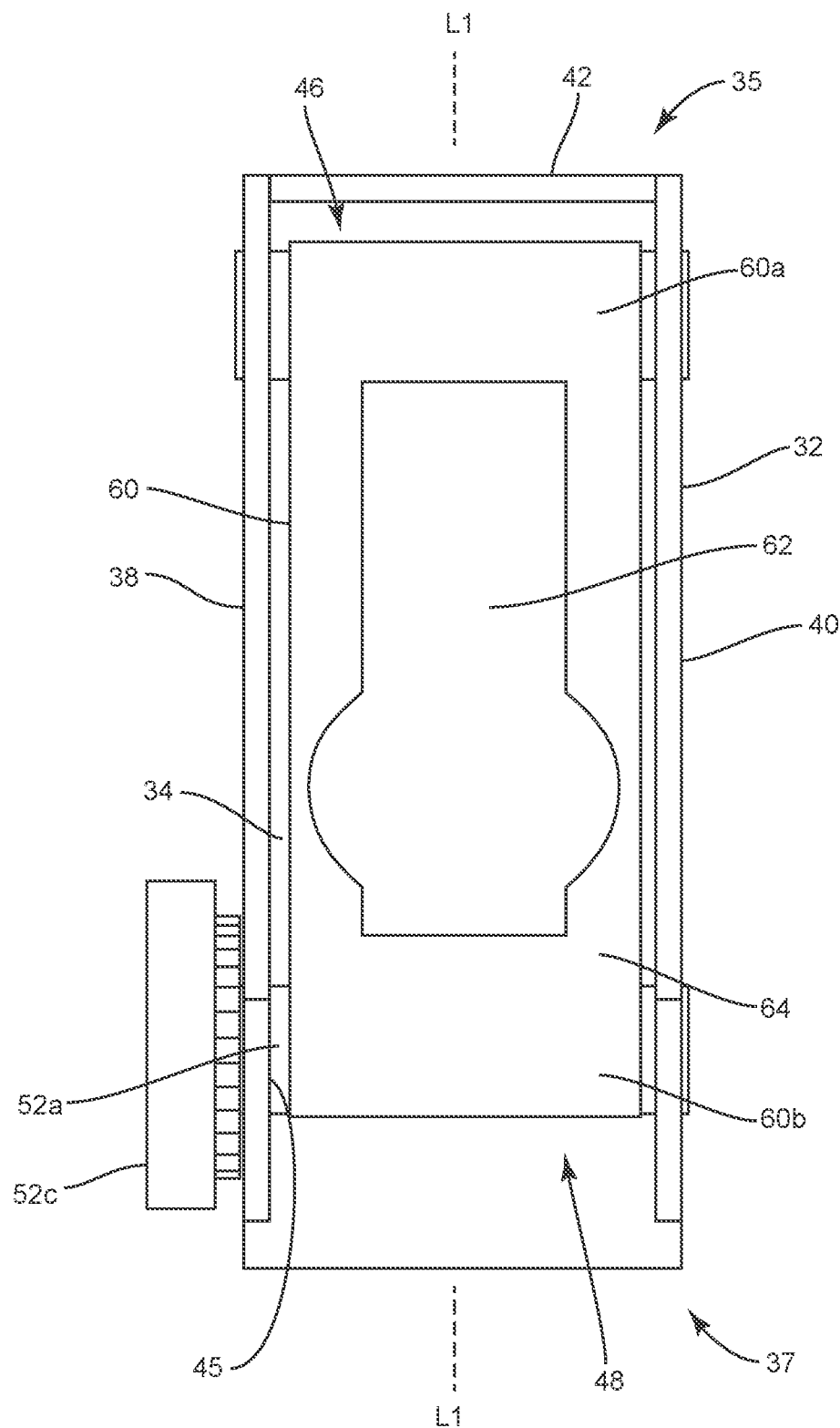
FIG. 5 is a top view of the dispensing system shown in FIG. 1.
Figure 6:
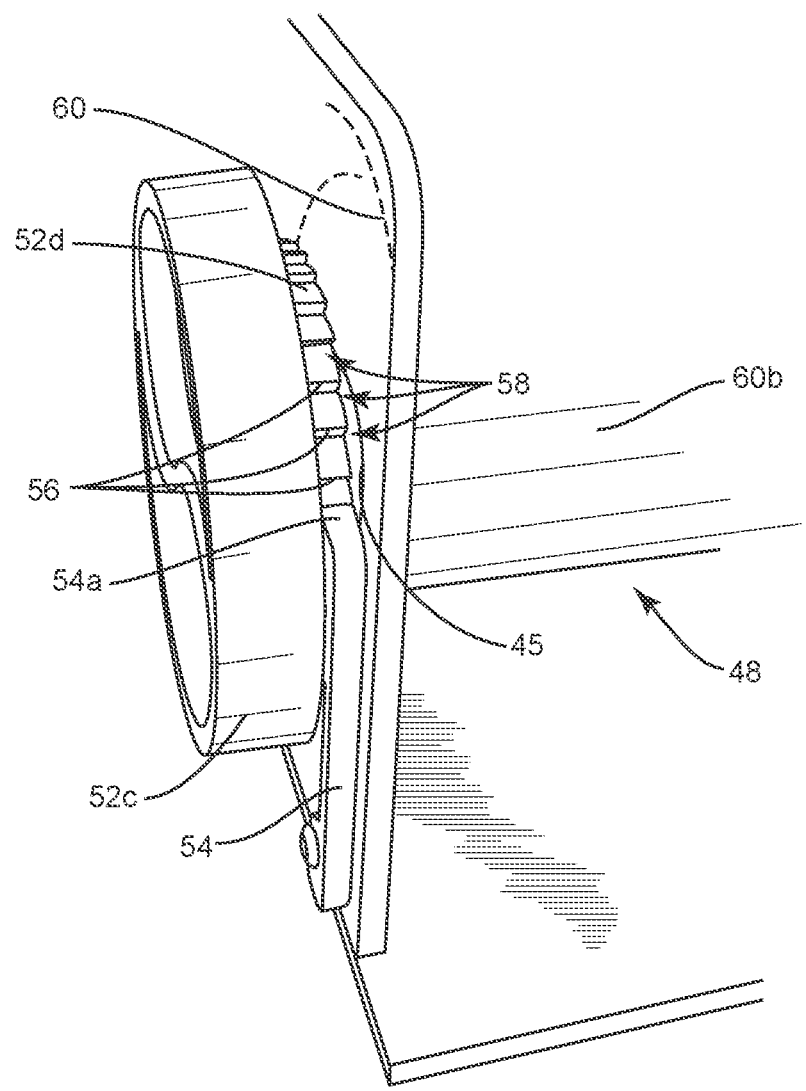
FIG. 6 is a perspective view of components of the dispensing system shown in FIG. 1.
Figure 12:
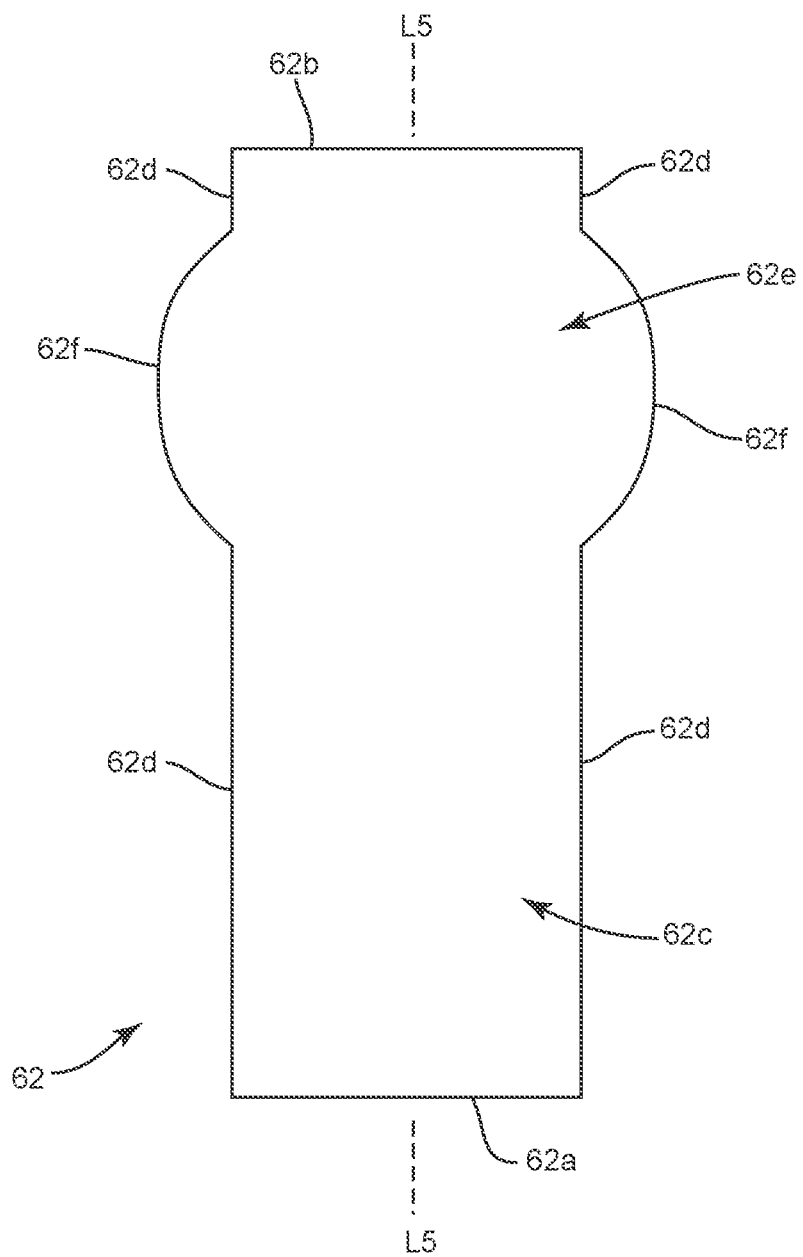
FIG. 12 is a top view of one embodiment of a component of the dispensing system shown in FIG. 1.
Figure 13:
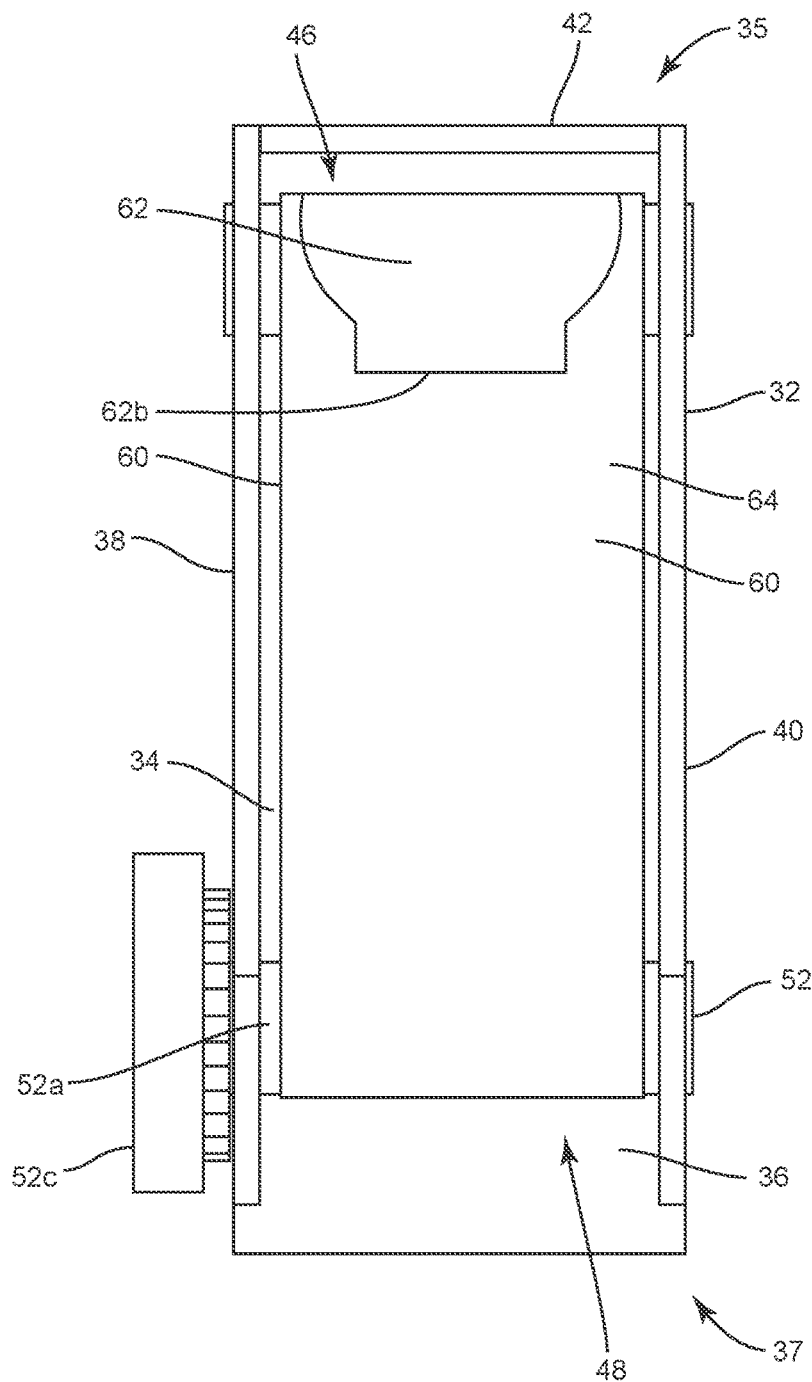
FIG. 13 is a top view of the dispensing system shown in FIG. 1.
Figure 14:
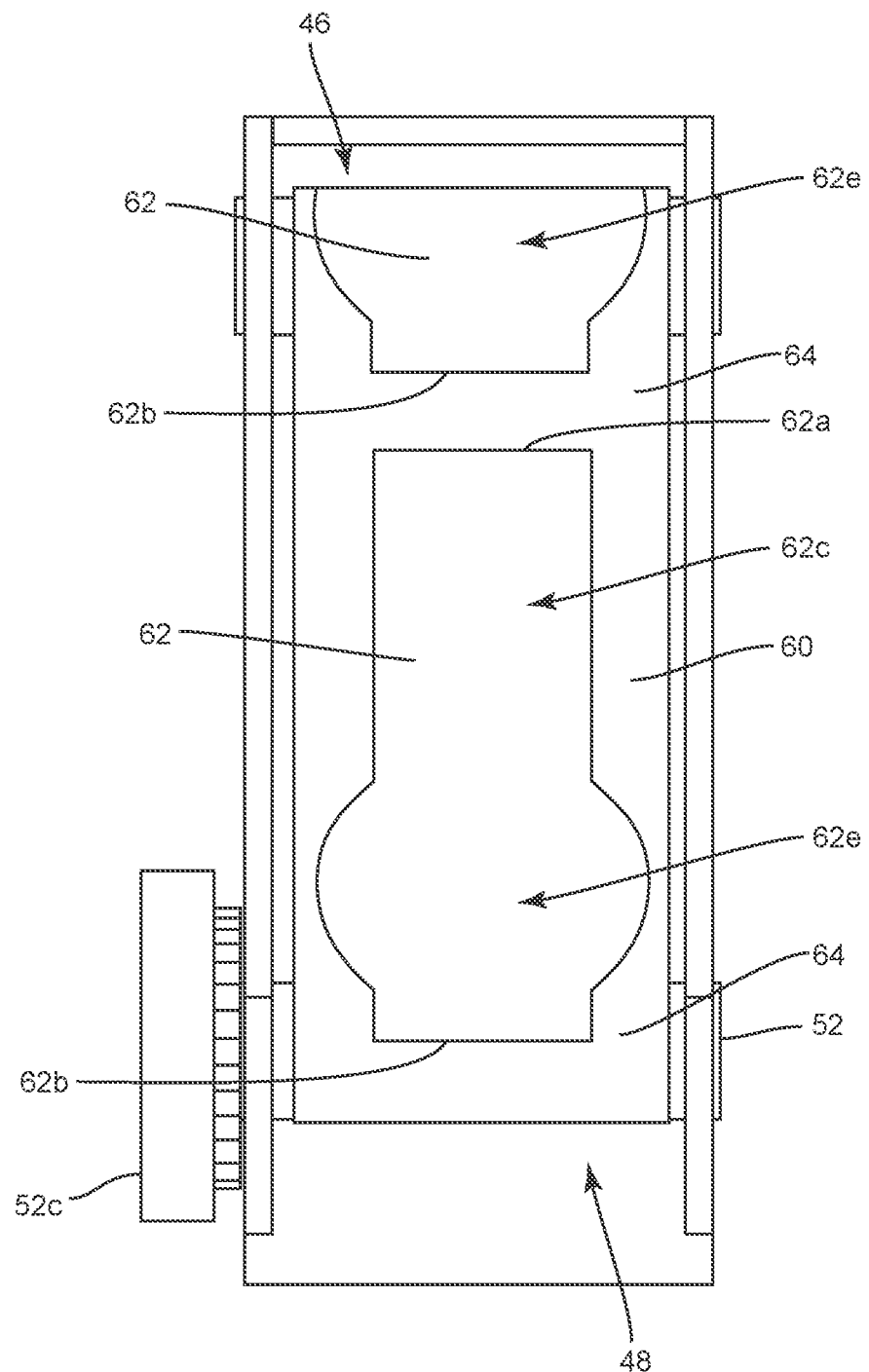
FIG. 14 is a top view of the dispensing system shown in FIG. 1.

A strip 60 is positioned on first and second rollers 50, 52 such that a first end 60a of strip 60 is wound about first roller 50 and an opposite second end 60b of strip 60 is wound about second roller 52. Strip 60 has a plurality of instrument covers 62 (FIGS. 10-12) positioned on a portion of strip 60, such as, for example, a first side 64 of strip 60, as discussed herein. Strip 60 is positioned relative to housing 32 and/or first and second rollers 50, 52 such that first end 60a of strip 60 extends through first opening 46 and second end 60b of strip 60 extends through second opening 48. In some embodiments, a portion of strip 60, such as, for example, an opposite second side 66 of strip 60 engages an outer surface of housing 32, such as, for example, an outer surface of top wall 34 when the portion of strip 60 is positioned between first and second openings 46, 48. In some embodiments, at least one of instrument covers 62 is positioned between first and second openings 46, 48 when the portion of strip 60 is positioned between first and second openings 46, 48, as shown in FIGS. 13 and 14. In some embodiments, only one instrument cover 62 is positioned between first and second openings 46, 48 when the portion of strip 60 is positioned between first and second openings 46, 48, as shown in FIG. 5, for example. In some embodiments, an entire instrument cover 62 and a portion of another instrument cover 62 are positioned between first and second openings 46, 48 when the portion of strip 60 is positioned between first and second openings 46, 48, as shown in FIG. 14.

In some embodiments, a portion of first end 60a of strip 60, such as, for example, an end surface of first end 60a of strip 60 is fixed to first roller 50 and a portion of second end 60b of strip 60, such as, for example, an end surface of second end 60b of strip 60 is fixed to second roller 52. As discussed above, first roller 52 is fixed relative to housing 32 and second roller 54 is rotatable relative to housing 32. This configuration allows strip 60 to be further wound about second roller 52 when second roller 52 is rotated relative to housing 32 about longitudinal axis L3 in one direction, such as, for example, direction C. That is, rotating second roller 52 relative to housing 32 about longitudinal axis L3 in one direction, such as, for direction C or direction D, will cause second end 60b of strip 60 to wind about second roller 52 such that more of strip 60 is wound about second roller 52 after second roller 52 is rotated relative to housing 32 about longitudinal axis L3 in the one direction than before second roller 52 is rotated relative to housing 32 about longitudinal axis L3 in the one direction. As such, a physician or medical provider can selectively advance strip 60 relative to housing such that one or more instrument covers 62 are positioned between first and second openings 46, 48 of housing 32. After an instrument cover 62 between first and second openings 46, 48 of housing 32 is applied to an instrument, such as, for example, a stethoscope, second roller 52 may be rotated relative to housing 32 about longitudinal axis L3 in the one direction to move strip 60 relative to housing 32 such that another instrument cover 62 is positioned between first and second openings 46, 48 of housing 32 so that the another instrument cover 62 can be applied to another instrument.

In some embodiments, rotating second roller 52 relative to housing 32 about longitudinal axis L3 in a second direction, such as, for example, direction D causes strip 60 to unwind from second roller 52. That is, rotating second roller 52 relative to housing 32 about longitudinal axis L3 in one direction, such as, for direction C or direction D, will cause second end 60b of strip 60 to unwind from second roller 52 such that less of strip 60 is wound about second roller 52 after second roller 52 is rotated relative to housing 32 about longitudinal axis L3 in the second direction than before second roller 52 is rotated relative to housing 32 about longitudinal axis L3 in the second direction.

In some embodiments, rotation of second roller 52 relative to housing 32 about longitudinal axis L3 in direction C and/or direction D may be automated by a device such as, for example, an actuator. It is envisioned that the actuator may be external of or internal to housing 32. In some embodiments, the actuator may be positioned inside or outside of cavity 44. In some embodiments, the actuator is configured to rotate second roller 52 such that one instrument cover 62 advances through first opening 46 and then stops rotating before the one instrument cover 62 advances through second opening 48 to position the one instrument cover 62 between first and second openings 46, 48. In some embodiments, the actuator begins to rotate second roller 52 in response to a sound such as, for example, a signal or voice command. In some embodiments, the actuator begins to rotate second roller 52 in response to motion. These configurations allow dispensing system 30 to dispense a single instrument cover 62 without the physician or medical provider touching any part of dispensing system 30.

In some embodiments, instrument covers 62 are configured to be applied to a portion of a stethoscope 68 (FIGS. 15-17), such as, for example, a head 70 of stethoscope 68 to prevent cross-contamination between stethoscope 68 and a patient, while still allowing stethoscope 68 to function properly. That is, instrument covers 62 do not inhibit and/or reduce the ability of a physician or medical provider to listen to internal sounds of an animal or human body using stethoscope 68. In some embodiments, instrument covers 62 are disposable. That is, instrument covers 62 are each configured for one-time use with a single patient such that a physician or medical provider covers at least a portion of stethoscope 68 with a first instrument cover 62. After examination is complete, the first instrument cover 62 may be removed from stethoscope 68 and discarded. The physician or medical provider may cover at least a portion of the same stethoscope 68 with a second instrument cover 62 before examining a second patient. This configuration reduces and/or prevents contamination from the first patient to the second patient.

In some embodiments, instrument covers 62 each comprise a material that is acoustically transmissive and substantially impermeable to microorganisms and fluids. In some embodiments, instrument covers 62 each comprise polyvinyl chloride, polyvinylidene chloride, low density polyethylene, linear low density polyethylene, polyisobutene, poly[ethylene-vinylacetate copolymer, lightweight aluminum foil and combinations thereof. In some embodiments, instrument covers 62 each comprise a crimpable material configured to form-fit around at least head 70 of stethoscope 68. In some embodiments, instrument covers 62 each comprise a first side that engages second side 66 of strip 60 and an opposite second side comprising an adherent material configured to allow the second sides of instrument covers 62 to adhere to a portion of stethoscope 68. In some embodiments, the thickness of each instrument cover 62 is in the range of from about 0.01 mm to about 0.8 mm. In some embodiments, instrument covers 62 each have a thickness in the range of from about 0.1 mm to about 0.4 mm. In some embodiments, dispensing system includes one or a plurality of stethoscopes, such as, for example, stethoscopes 68.

In some embodiments, the first sides of instrument covers 62 that contacts strip 62 is sprayed or coated with a material having non-stick properties and/or is glossy to prevent the material having adhesion and/or adherent properties and/or the first sides of instrument covers 62 from sticking to first side 64 of strip 60. In some embodiments, the material having non-stick properties forms the first sides of instrument covers 62. That is, the material having non-stick properties is integrally formed with the first sides of instrument covers 62 to provide the first sides of instrument covers 62 with non-stick properties. In some embodiments, the first sides of instrument covers 62 are coated with a powder to prevent the first sides of instrument covers 62 from permanently sticking to first side 64 of strip 60. In some embodiments, the first sides of instrument covers 62 are sprayed or coated with an agent comprising wax to prevent the first sides of instrument covers 62 from permanently sticking to first side 64 of strip 60. In some embodiments, at least one of the first and second sides of instrument covers 62 comprises an antimicrobial substance that can neutralize or destroy microbes. In some embodiments, at least first side 64 of strip 60 and/or at least the first sides of instrument covers 62 are made of a material that allows static electricity to form that causes instrument covers 62 to stick to first side 64 of strip 60.

Figure 3:
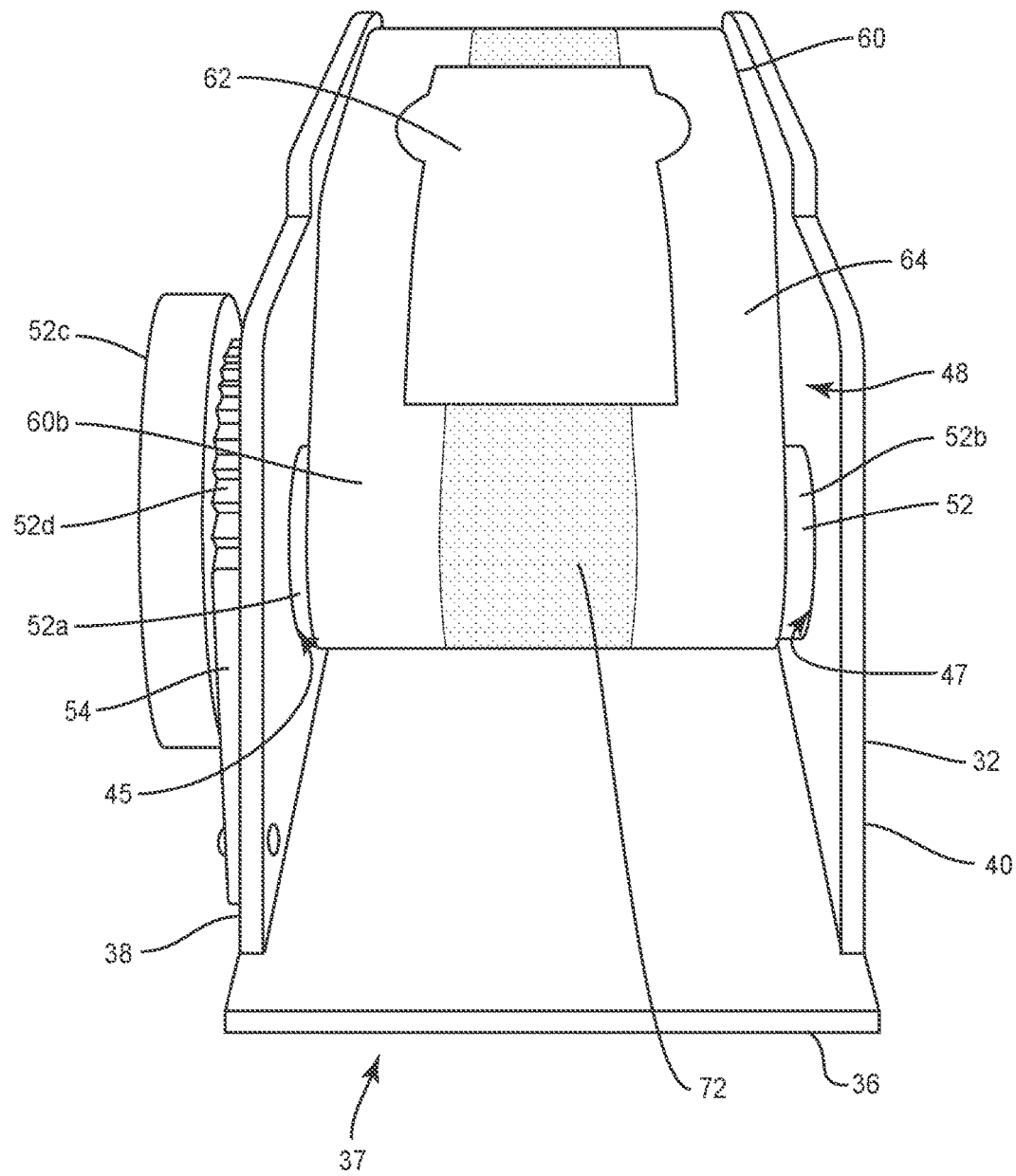
FIG. 3 is a front view of the dispensing system shown in FIG. 1.

In some embodiments, the first sides of instrument covers 62 are free of any adhesive material and first side 64 of strip 60 includes an adhesive 72 (FIG. 3) sprayed or coated on first side 64 to allow instrument covers 62 to adhere to first side 64. As shown in FIG. 3, adhesive 72 is applied to strip 60 in a manner such that adhesive 72 forms a central stripe of adhesive material that extends the entire length of strip. In some embodiments, the first sides of instrument covers 62 are made of a material that allows static electricity to form that causes instrument covers 62 to stick to first side 64 of strip 60 and first side 64 of strip 60 includes adhesive 72 sprayed or coated on first side 64, thus providing a dual means to removably adhere instrument covers 62 to strip 60. In some embodiments, first side 64 of strip 60 are free of any adhesive material, such as, for example, adhesive 72.

In some embodiments, the second sides of instrument covers 62 are each made from and/or coated with a material having adhesion and/or adherent properties to allow instrument covers 62 to removably adhere to at least a portion of a stethoscope, such as, for example, head 70 of stethoscope 68. In some embodiments, the second sides of instrument covers 62 are sprayed or coated with the material having adhesion and/or adherent properties. In some embodiments, the material having adhesion and/or adherent properties forms the second sides of instrument covers 62. That is, the material having adhesion and/or adherent properties is integrally formed with instrument covers 62 to provide the second sides of instrument covers 62 with adhesion and/or adherent properties. The material having adhesion and/or adherent properties may include one or more of a cellophane, vinyl, acetate, polyethylene acrylic, butyl rubber, ethylene-vinyl acetate, natural rubber, a nitrile, silicone rubber, a styrene block copolymer, a vinyl ether and a tackifier. In some embodiments, the adhesive and/or adherent material further includes an antimicrobial and/or antiseptic material. Antiseptic materials that can be used include but are not limited to: alcohols such as ethanol, 1-propanol and 2-propanol/isopropanol or mixtures of these alcohols; sodium bicarbonate; hydrogen peroxide; benzalkonium chloride; chlorohexidine; hexachlorophene; iodine compounds; and combinations thereof. Antimicrobial materials that can be used include but are not limited to: beta-lactam antibiotics (such as penicillin, cephalosporin); protein synthesis inhibitors (such as aminoglycosides, macrolides, tetracycline, chloramphenicol, polypeptides); sulphonamides; cotrimoxazole; quinolones; anti-viral agents; anti-fungal agents; anti-cancer drugs; anti-malarial drugs; anti-tuberculosis drugs; anti-leprotic drugs; anti-protozoal drugs; and combinations thereof. In some embodiments, the antimicrobial material is at least partially removable so that at least a portion of the antimicrobial material is left behind as covers 62 are removed from a medical device or instrument, such as, for example, a stethoscope. In some embodiments, the material having adhesion and/or adherent properties is sprayed or coated with weak adhesive non-toxic glue, such as, for example, spirit gum, when additional adherency is desired. That is, the amount of adherency may be adjusted by coating or spraying the material having adhesion and/or adherent properties with the weak adhesive. In embodiments in which the material having adhesion and/or adherent properties is coated or sprayed onto the second sides of instrument covers 62, it is envisioned that the material having adhesion and/or adherent properties may be sprayed or coated with one or more layers of the weak adhesive before or after the material having adhesion and/or adherent properties is applied to the second sides of instrument covers 62, the one or more layers of the weak adhesive may be sprayed onto the material before the material is formed into the second sides of instrument covers 62. In some embodiments, the second sides of instrument covers 62 each comprise a material that accumulates static electricity to impart the second sides of instrument covers 62 with adhesion and/or adherent properties.

In some embodiments, the second sides of instrument covers 62 each include a plurality of concentric circles to help direct sound internal sounds of an animal or human body to a stethoscope, such as, for example, stethoscope 68. In some embodiments, at least one of the first and second sides of instrument covers 62 each include a plurality of concentric circles. The concentric circles can include one or more circles within an outer circle. In some embodiments, the concentric circles are imprinted on instrument covers 62. In some embodiments, the concentric circles are embossed on instrument covers 62. In some embodiments, instrument covers 62 each have a first maximum thickness and portions of instrument covers 62 that define the concentric circles have a thickness that is less than the maximum thickness.

In some embodiments, instrument covers 62 are spaced apart from one another along strip 60. That is, instrument covers 62 do not contact one another. In some embodiments, instrument covers 62 define an elongated band or segment, wherein one instrument cover 62 is connected to another instrument cover 62 by a zone of weakness, such as, for example, a series of perforations. In some embodiments, the perforations extend through the first and second sides of each instrument cover 62. In some embodiments, the perforations have a substantially rectangular or square configuration and are uniformly spaced apart from one another. In some embodiments, the perforations include a single perforation that extends the entire distance between opposite side surfaces of each of instrument covers 62. In some embodiments, the perforations may be variously configured and dimensioned, such as, for example, oval, oblong, triangular, square, polygonal, irregular, uniform, non-uniform, offset, staggered, undulating, arcuate, variable and/or tapered, depending on the requirements of a particular application.

In some embodiments, instrument covers 62 are each sized so that they each cover the head of a standard stethoscope, such as for example head 70 of stethoscope 68. In some embodiments, instrument covers 62 are each sized to cover at least a portion of a diaphragm 74 of stethoscope 68, at least a portion of head 70 and at least a portion of tubing 76 attached to head 70 to transfer sound to ear pieces of stethoscope 68. In some embodiments, instrument covers 62 are each sized to at least a portion of head 70 and at least a portion of tubing 76, without covering any portion of diaphragm 74 of stethoscope 68. In some embodiments, instrument covers 62 are each about 4 inches by about 6 inches, 3 inches by about 5 inches, 2.5 inches by 4 inches, as well as any size in between. It is contemplated that various sizes can be available according to the type of medicine being practiced. For example, instrument covers 62 for a pediatric stethoscope may be smaller in size than instrument covers 62 for a stethoscope used for adults.

Figure 10:
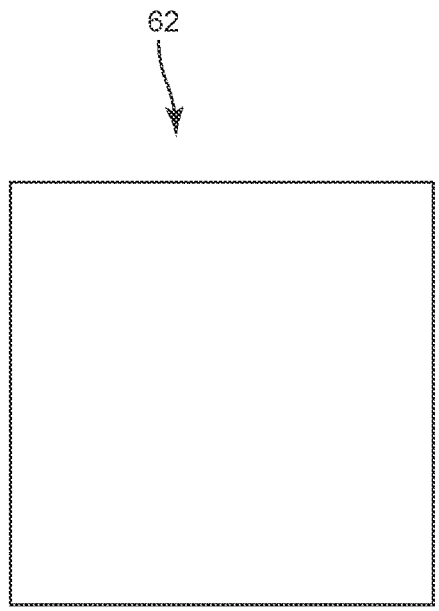
FIG. 10 is a top view of one embodiment of a component of the dispensing system shown in FIG. 1.
Figure 11:
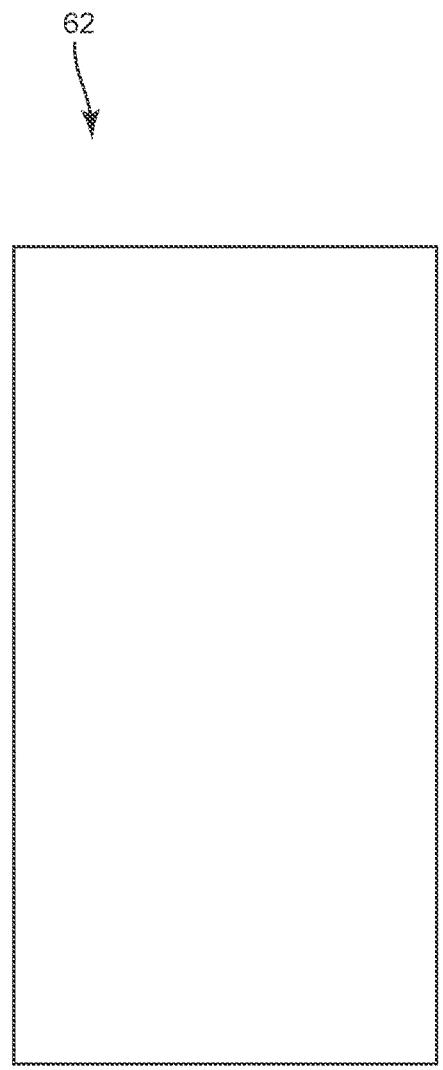
FIG. 11 is a top view of one embodiment of a component of the dispensing system shown in FIG. 1.
Figure 15:
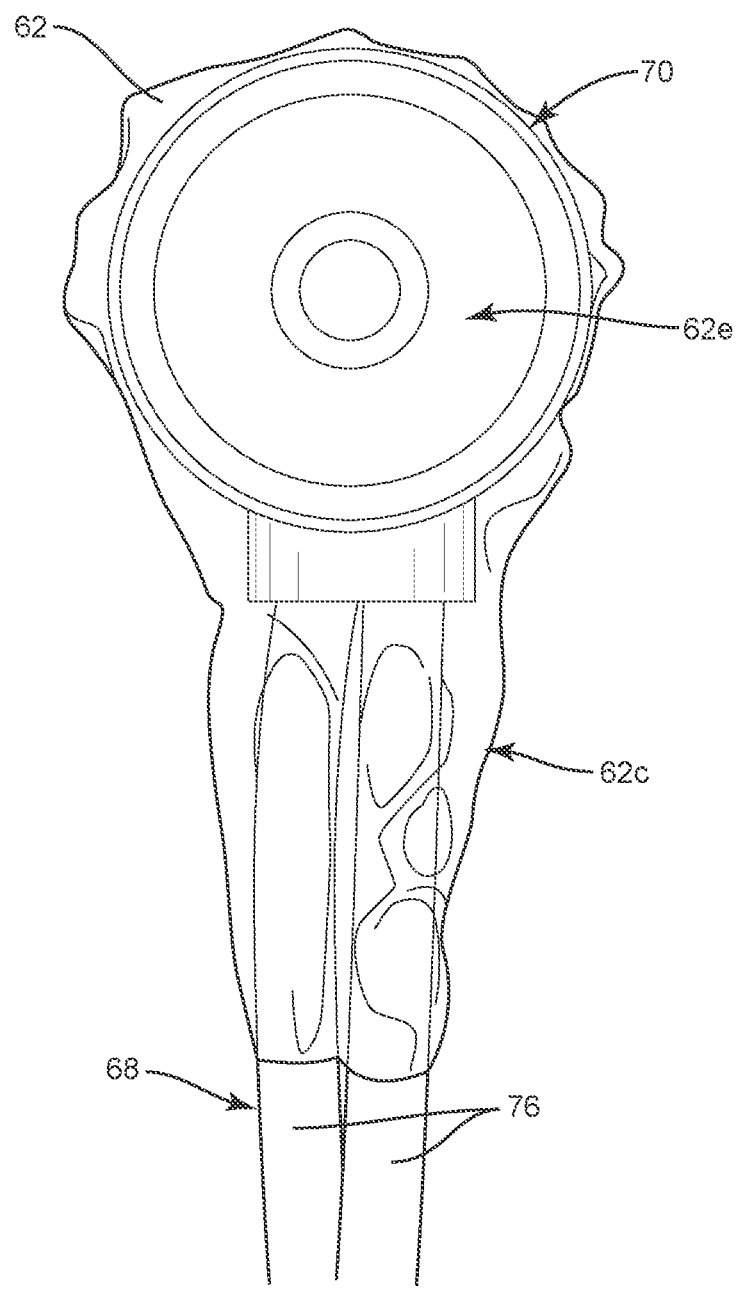
FIG. 15 is a top view of components of the system shown in FIG. 1.
Figure 16:
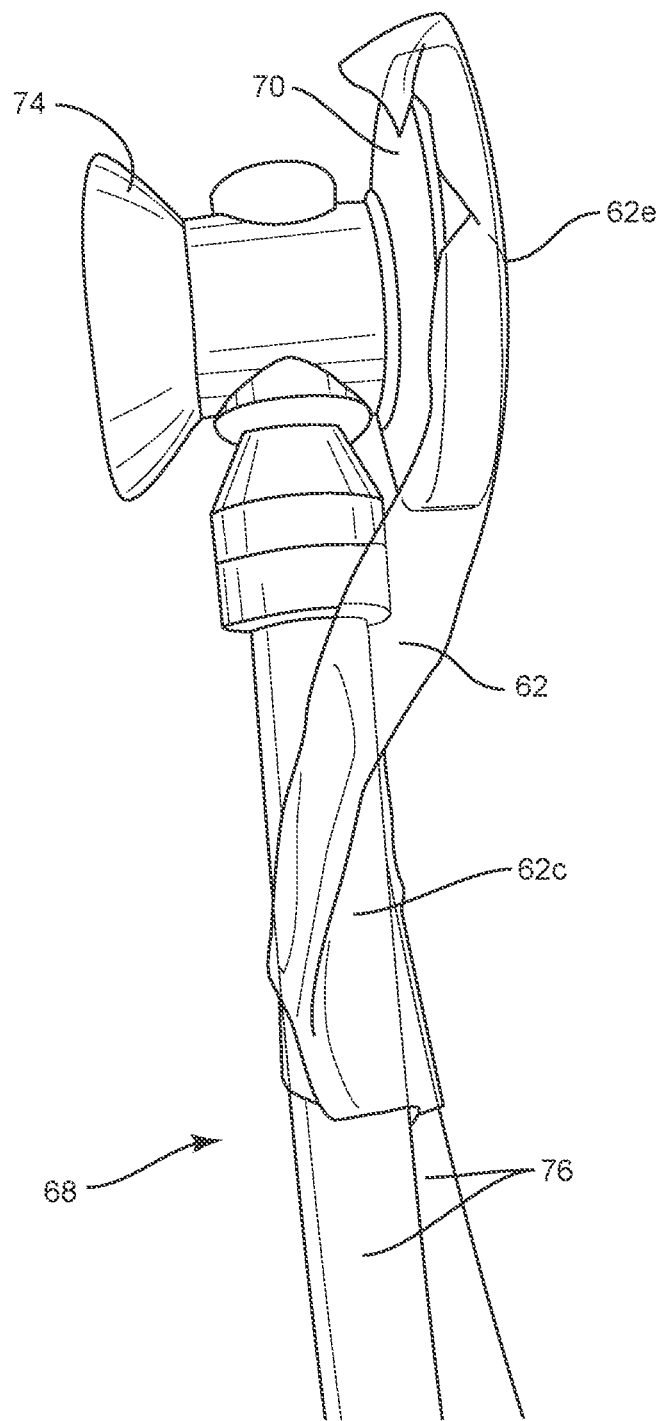
FIG. 16 is a side view of components of the system shown in FIG. 1.
Figure 17:
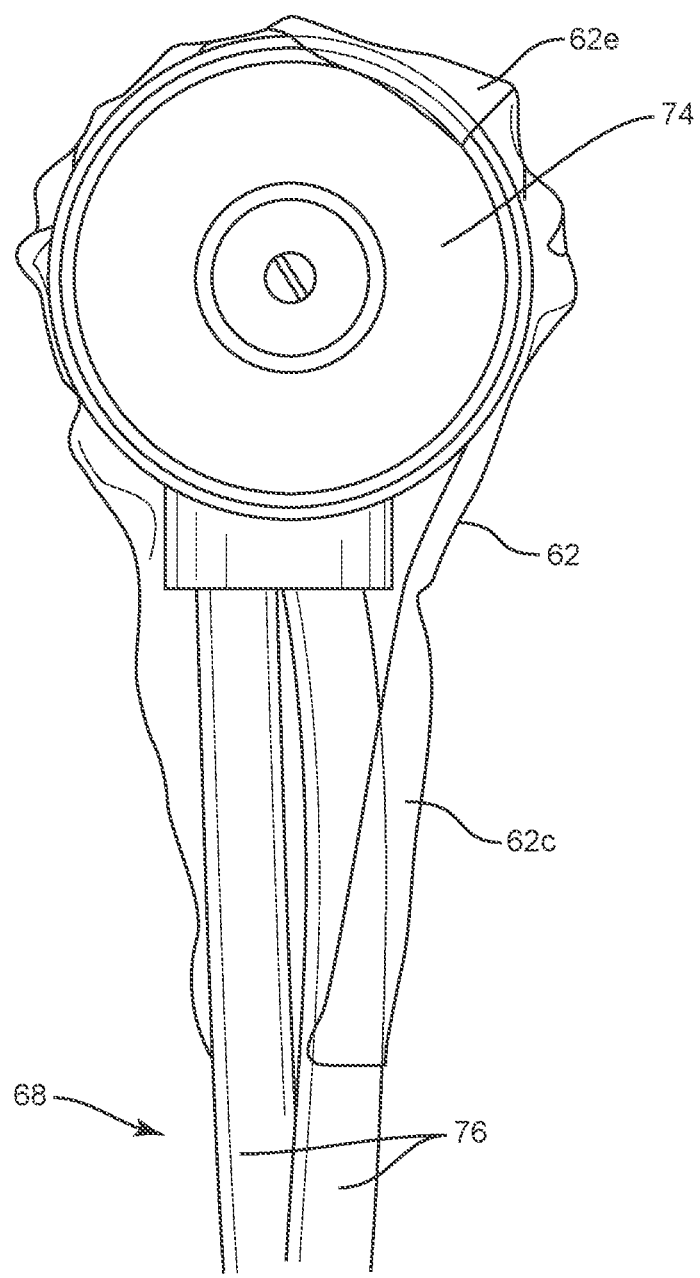
FIG. 17 is a bottom view of components of the system shown in FIG. 1.
Figure 18:
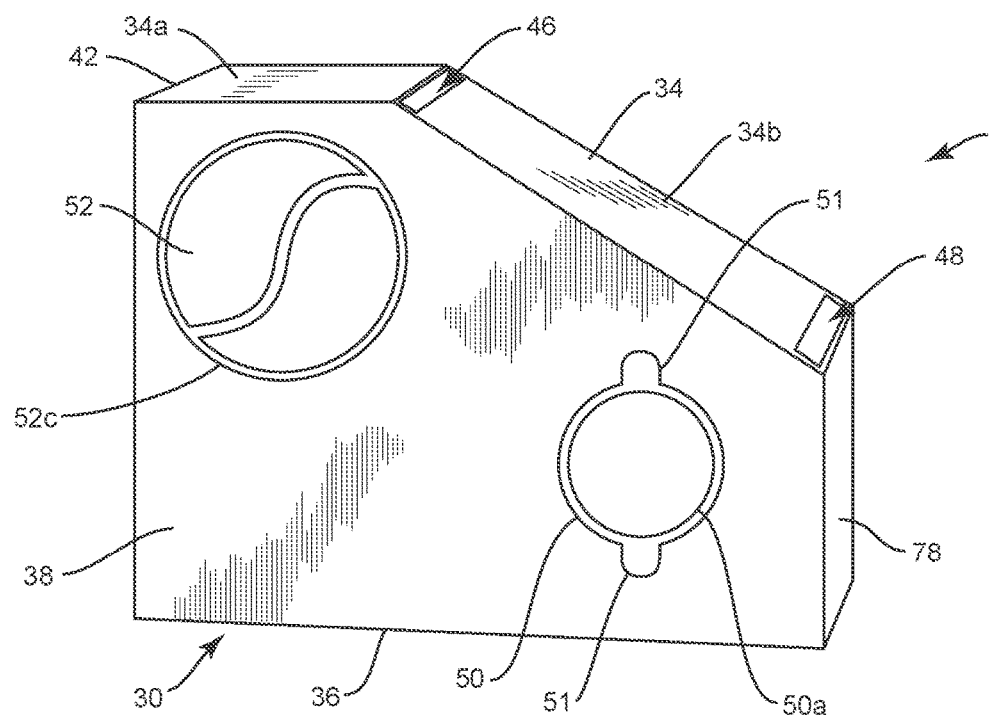
FIG. 18 is a side view of one embodiment of components of a dispensing system in accordance with the principles of the present disclosure.
Figure 19:
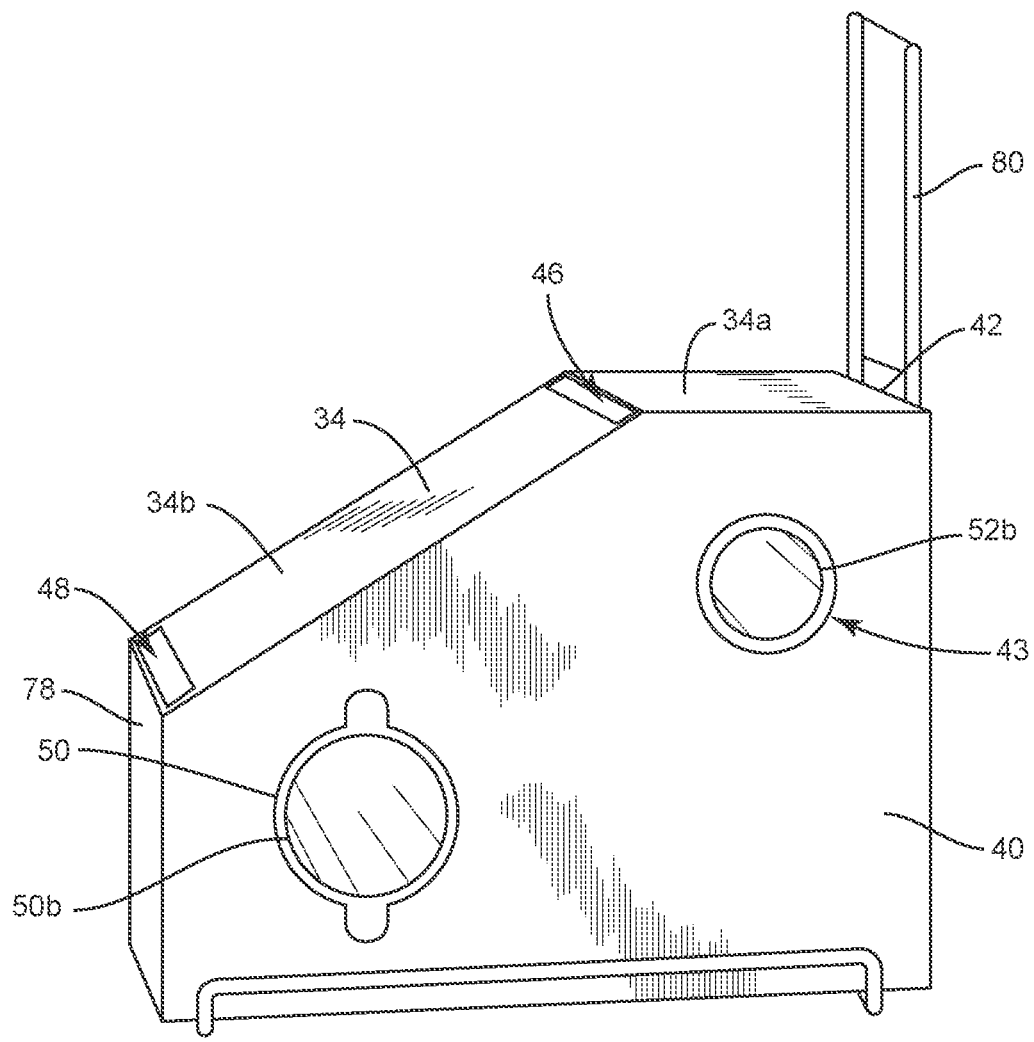
FIG. 19 is a side view of components of the dispensing system shown in FIG. 18.
Figure 20:
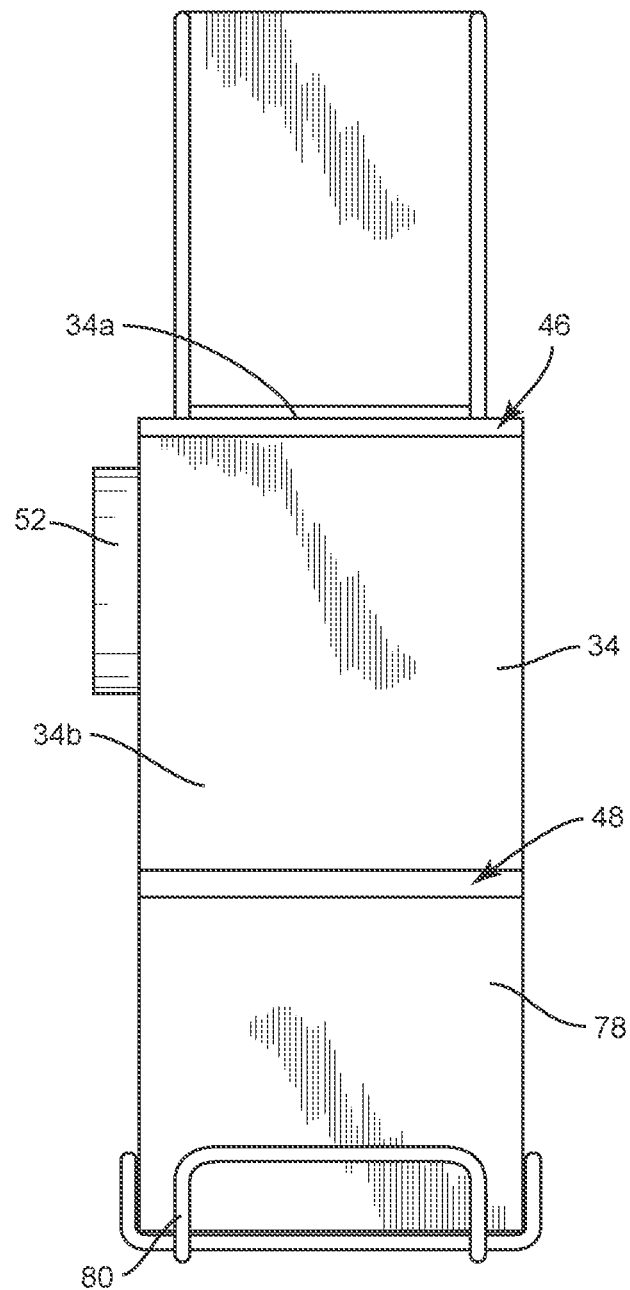
FIG. 20 is a front view of components of the dispensing system shown in FIG. 18.

In some embodiments, stethoscope covers 62 each have a square configuration, as shown in FIG. 10. In some embodiments, stethoscope covers 62 each have a rectangular configuration, as shown in FIG. 11. In some embodiments, stethoscope covers 62 each extend along a longitudinal axis L5 between a first end 62a and an opposite second end 62b, as shown in FIG. 12. Instrument cover 62 includes opposite sidewalls 62d that each extend parallel to longitudinal axis L5. First end 62a includes a first section 62 and second end 62b of instrument cover 62 includes a second section 62e having opposite sidewalls 62f that bow outwardly from sidewalls 62d. Second section 62e has a size and shape configured to cover head 70 of stethoscope 68 while first section 62 is wrapped about at least a portion of tubing 76 of stethoscope 68, as shown in FIGS. 15-17.

In assembly, operation and use, a physician or medical provider can advance first end 60a of strip 60 such that one instrument cover 62 that is wound about first roller 50 is positioned between first and second openings 46, 48 by rotating second roller 52 relative to housing 32 about longitudinal axis L3 in direction C or direction D, as discussed above. Second roller 52 may be rotated relative to housing 32 about longitudinal axis L3 either manually or via the actuator. When second roller 52 is rotated manually, the physician or medical provider may rotate second roller 52 by grasping gripping portion 52c with his or her hand and rotating second roller 52 in direction C or direction D.

As discussed above, the ratchet defined by ratchet portion 52d and pawl 54 allows second roller 52 to be rotated relative to housing 32 about longitudinal axis L3 in a manner that selectively advances strip 60 through first and second openings 46, 48 of housing such that the amount of a given instrument cover 62 that is positioned between first and second openings 46, 48 can be varied. For example, second roller 52 may be rotated relative to housing 32 about longitudinal axis L3 to move strip 60 from a first orientation, wherein there are no instrument covers 62 positioned between first and second openings 46, 48 of housing 32 or only a portion of one of instrument covers 60 is positioned between first and second openings 46, 48, shown in FIG. 13, to a second position, shown in FIG. 14, in which an entire instrument cover 62 is positioned between first and second openings 46, 48. That is, moving strip 60 from the first orientation to the second orientation advances strip 60 such that the entire instrument cover 62 shown in FIG. 13 is positioned between first and second openings 46, 48, as shown in FIG. 14.

Once instrument cover 62 is in a selected position, such as, for example the position shown in FIG. 14, the physician or medical provider can apply the instrument cover 62 that is positioned between first and second openings 46, 48 to stethoscope 68. In some embodiments, instrument cover 62 is applied to stethoscope 68 by positioning head 70 of stethoscope 68 over second section 62e of instrument cover 62 and moving head 70 to engage second section 62e. In some embodiments, a downward force is applied to head 70 to press strip 60 against the outer surface of top wall 34 of housing 32 such that instrument cover 62 is positioned between head 70 and strip 60. Head 70 may then be moved away from housing 32. Instrument cover 62 will adhere to head 70 upon contacting head 70 such that moving head 70 away from housing 32 removes instrument cover 62 from strip 60. In some embodiments, engaging head 70 with instrument cover 62 allows instrument cover 62 to adhere to head 70 to form a substantially air-tight seal with head 70. In some embodiments, instrument cover 62 is crimped about head 70. In some embodiments, first section 62c of instrument cover 62 is folded about tubing 76 of stethoscope 68 such that first section 62c adheres to tubing 76, as shown in FIGS. 15-17. In some embodiments, instrument cover 62 is crimped and/or folded about tubing 76. The physician or medical provider may then examine a first patient using stethoscope 68.

Prior to examining a second patient, the physician or medical provider may remove instrument cover 62 from stethoscope 68 to prevent any cross-contamination from the first patient from contaminating the second patient. Instrument cover 62 may be discarded. Once instrument cover is removed from stethoscope 68, second roller 52 may be rotated relative to housing 32 about longitudinal axis L3 to move strip 60 from the first orientation, shown in FIG. 13, to the second position, shown in FIG. 14. As second roller 52 moves from the first orientation to the second orientation, second end 60b of strip 60 winds further around second roller 52. The portion of strip 60 that winds around second roller 52 does not have any instrument covers 62 on strip 60, as they would have been removed by the physician or medical provider before second roller 52 is moved from the first orientation to the second orientation. The physician or medical provider may then apply the instrument cover 62 positioned between first and second openings 46, 48 to stethoscope 68 in the manner discussed above. The physician or medical provider may then examine a second patient using stethoscope 68. Instrument cover 62 may be discarded after the physician or medical provider examines the second patient. The steps discussed above may be repeated for each patient the physician or medical provider examines to prevent cross-contamination between patients.

In some embodiments, shown in FIGS. 18-22, housing 32 comprises a front wall 78 opposite rear wall 42. Front wall 78 extends parallel to rear wall 42. First roller 50 extends through openings 45, 47 and second roller 52 extends through openings 41, 43 such that second roller 52 is positioned between rear wall 42 and first roller 50. This is the reverse of the embodiments shown in FIGS. 1-9, 13 and 14, in which first roller 50 extends through openings 41, 43 and second roller 52 extends through openings 45, 47 such that first roller 50 is positioned between rear wall 42 and second roller 52.

In the embodiment shown in FIGS. 18-22, top wall 34 includes a first section 34a that is separated from a second section 34b of top wall 34 by first opening 46. First section 34a extends parallel to bottom wall 36 and second section 34b extends transverse to bottom wall 36 and first section 34a. Second section 34b is spaced apart from front wall 78 by second opening 48. This configuration allows strip 60 to be positioned on an inclined surface defined by second section 34b when strip 60 is positioned through first and second openings 46, 48.

In some embodiments, system 30 includes a bracket 80 (FIGS. 19-21) that mounts directly to the vertical surface and/or the horizontal surface. Housing 32 is positioned within bracket 80 to fix housing 32 relative to the vertical surface and/or horizontal surface.

Figure 21:
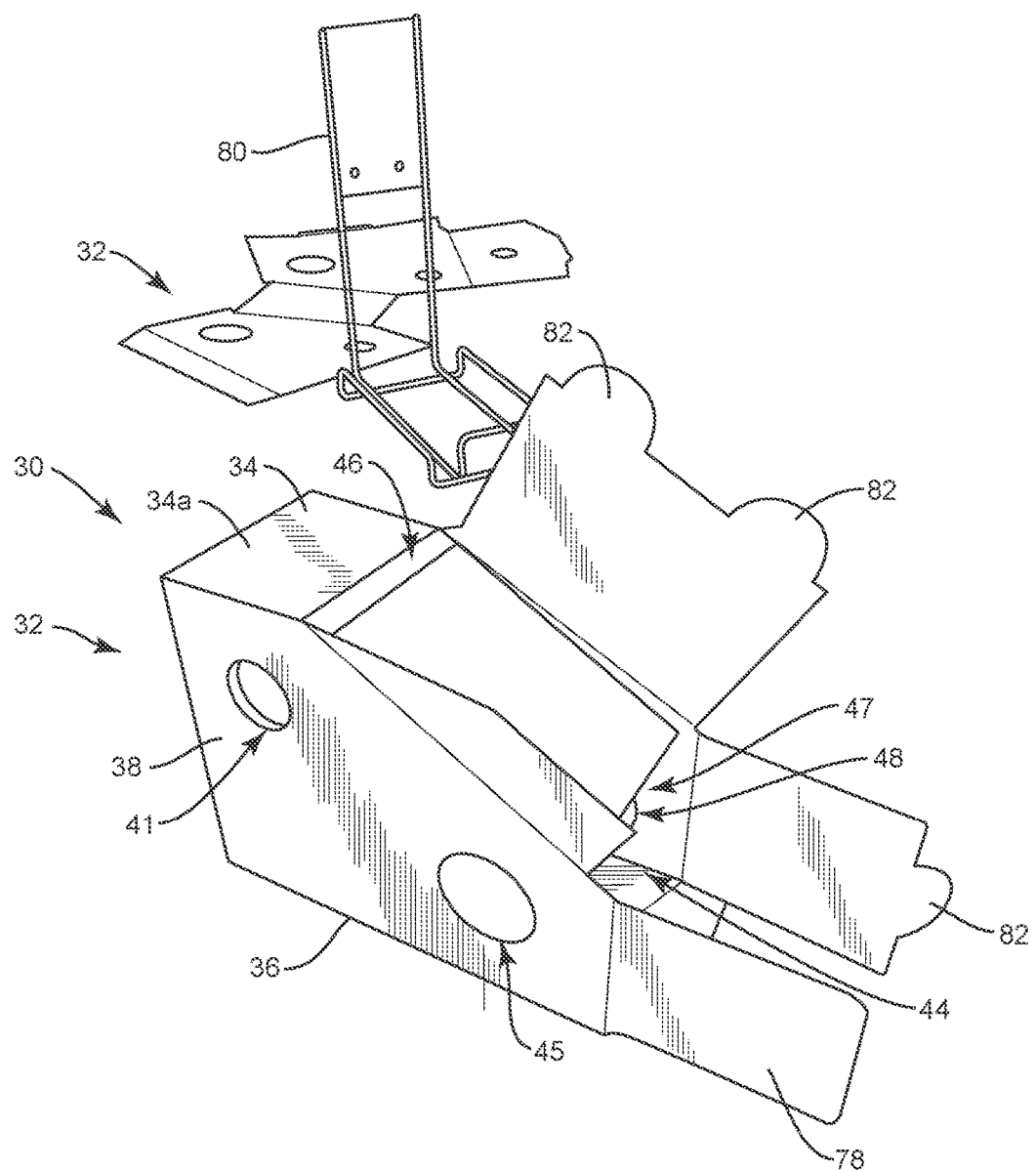
FIG. 21 is a perspective view of components of the dispensing system shown in FIG. 18.
Figure 22:
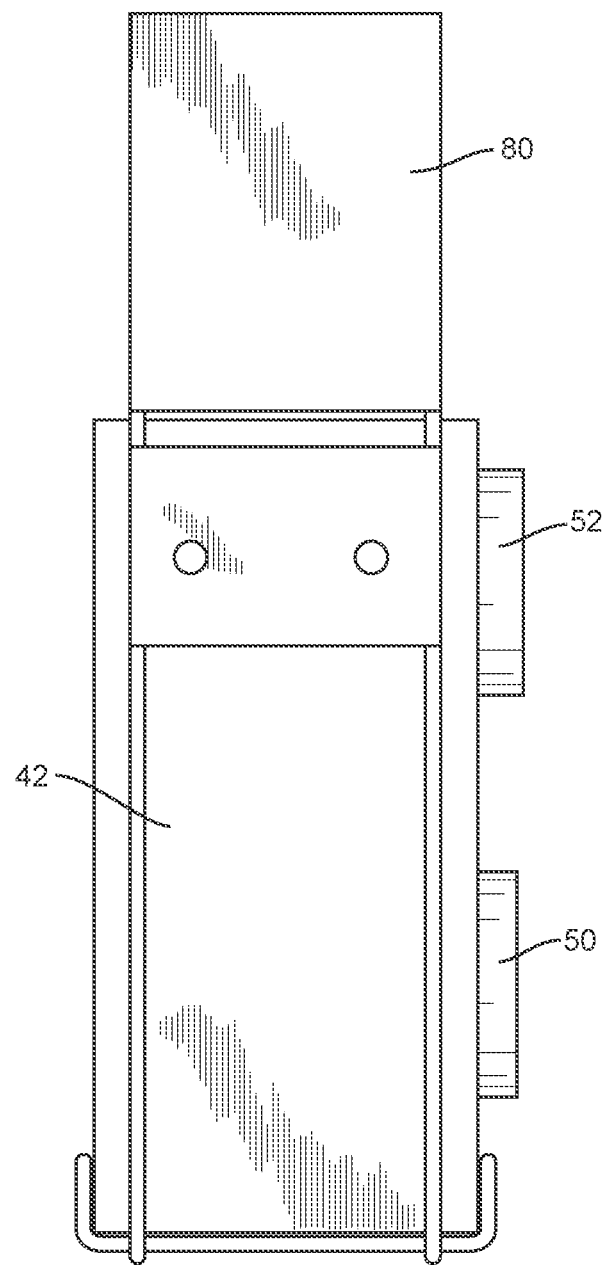
FIG. 22 is a rear view of components of the dispensing system shown in FIG. 18.

In some embodiments, housing 32 is constructed of a single piece of material, as shown in FIG. 21. In some embodiments, housing 32 is constructed of a single piece of material, such as, for example, cardboard. The single piece of material includes folds that allow the single piece of material to be folded to form housing 32. In some embodiments, the single piece of material is a flat piece of material, as shown in FIG. 21, that is folded to form housing 32. In some embodiments, the single piece of material includes tabs 82 (FIG. 21) that allow housing 32 to remain in the folded configuration. In some embodiments, tabs 82 are positioned in apertures in housing 32 to allow housing 32 to remain in the folded configuration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The embodiments above can also be modified so that some features of one embodiment are used with the features of another embodiment. One skilled in the art may find variations of these embodiments, which, nevertheless, fall within the spirit of the present disclosure, whose scope is defined by the claims set forth below.

What is claimed is:

1. A dispensing system comprising;
    a housing comprising opposite top and bottom walls, opposite first and second side walls that each extend between the top and bottom walls, a cavity, a first opening and a second opening, the cavity having a maximum height defined by a distance from an inner surface of the top wall to an inner surface of the bottom wall, the openings being in communication with the cavity;
    a pawl comprising a first end that is coupled to the housing and a second end including a projection;
    a first roller positioned within the cavity;
    a second roller extending parallel to the first roller, the second roller being positioned within the cavity, the second roller comprising a gripping portion and a ratchet portion, the gripping portion, the pawl and the ratchet portion being positioned outside of the cavity, the ratchet portion comprising a plurality of angled teeth disposed circumferentially about the ratchet portion, the teeth engaging the projection such that the second roller may be rotated in a first direction and is prevented from being rotated in an opposite second direction;
    a strip extending through the openings, the strip having a first end that is wound about the first roller, a second end that is wound about the second roller and an intermediate portion that directly engages an outer surface of the top wall that is opposite the inner surface of the top wall; and
    a plurality of instrument covers removably positioned on the strip,
    wherein the top wall has a maximum length defined by a distance from a front edge of the top wall to a back edge of the top wall, the front edge being positioned between the rollers.

2. A dispensing system as recited in claim 1, wherein the first roller is fixed relative to the housing to prevent rotation of the first roller relative to the housing.

3. A dispensing system as recited in claim 1, wherein the intermediate portion of the strip comprises at least one of the instrument covers.

4. A dispensing system as recited in claim 1, wherein a portion of the first end of the strip that is wound around the first roller comprises at least one of the instrument covers and a portion of the second end of the strip that is wound about the second roller is free of the instrument covers.

5. A dispensing system as recited in claim 1, wherein the openings extend through the top wall.

6. A dispensing system as recited in claim 1, wherein a portion of the first end of the strip is fixed to the first roller and a portion of the second end of the strip is fixed to the second roller.

7. A dispensing system as recited in claim 1, wherein the teeth are angled in a direction that allows the second end of the strip to be further wound about the second roller when the second roller is rotated in the first direction.

8. A dispensing system as recited in claim 1, wherein the instrument covers each comprise a crimpable material configured to form-fit around at least a head of a stethoscope.

9. A dispensing system as recited in claim 1, wherein the instrument covers each comprise a first side that engages the strip and an opposite second side comprising an adherent material configured to allow the second side to adhere to a portion of a stethoscope.

10. A dispensing system as recited in claim 1, wherein the instrument covers each extend along a longitudinal axis between a first end and a second end, the first end of the instrument cover comprising a first section having opposite sidewalls that extend parallel to the longitudinal axis, the second end of the instrument cover comprising a second section having opposite sidewalls that bow outwardly from the sidewalls of the first section, the second section having a size and shape configured to cover a head of a stethoscope.

11. A dispensing system as recited in claim 1, wherein the projection is biased relative to the housing to prevent the second roller from being rotated in the second direction.

12. A dispensing system as recited in claim 1, wherein the ratchet portion is a disc, the teeth extending from an outer surface of the disc.

13. A dispensing system as recited in claim 1, wherein the pawl is deflectable relative to the housing.

14. A dispensing system as recited in claim 1, wherein the projection is fixed relative to the second end of the pawl.

15. A dispensing system as recited in claim 1, wherein the instrument covers each include a plurality of concentric circles configured to direct internal sounds of an animal or human body to a stethoscope.

16. A dispensing system as recited in claim 1, wherein the instrument covers are spaced apart from one another along the strip.

17. A dispensing system as recited in claim 1, wherein the back edge is positioned between the first roller and a back wall of the housing that connects the first side wall with the second side wall.

18. A dispensing system as recited in claim 9, wherein the first side comprises a material that allows the first side to stick to the strip due static cling created by at least one of the first side and the strip.

19. A stethoscope covering system comprising:
  a dispensing system comprising:
    a housing comprising opposite top and bottom walls, opposite first and second side walls that each extend between the top and bottom walls, a cavity, a first opening and a second opening, the cavity having a maximum height defined by a distance from an inner surface of the top wall to an surface of the bottom wall, the openings being in communication with the cavity,
    a pawl comprising a first end that is coupled to the housing and a second end including a projection,
    a first roller positioned within the cavity, the pawl being coupled to the housing via a pin that extends parallel to the first roller,
    a second roller extending parallel to the first roller, the second roller being positioned within the cavity, the second roller comprising a gripping portion and a ratchet portion, the gripping portion, the pawl and the ratchet portion being positioned outside of the cavity, the ratchet portion comprising a plurality of angled teeth disposed circumferentially about the ratchet portion, the teeth engaging the projection such that the second roller may be rotated in a first direction and is prevented from being rotated in an opposite second direction,
    a strip extending through the openings, the strip having a first end that is wound about the first roller, a second end that is wound about the second roller and an intermediate portion that directly engages an outer surface of the top wall that is opposite the inner surface of the top wall, and
    a plurality of instrument covers positioned on one side of the strip; and
  at least one stethoscope comprising a head,
  wherein the instrument covers are each configured to completely cover the head, and
  wherein the top wall has a maximum length defined by a distance from a front edge of the top wall to a back edge of the top wall, the front edge being positioned between the rollers.

20. A kit comprising:
  a dispensing system comprising:
    a housing comprising opposite top and bottom walls, opposite first and second side walls that each extend between the top and bottom walls, a cavity, a first opening and a second opening, the cavity having a maximum height defined by a distance from an inner surface of the top wall to an inner surface of the bottom wall, the openings being in communication with the cavity,
    a pawl comprising a first end that is coupled to the housing and a second end including a projection,
    a first roller positioned within the cavity, the pawl being coupled to the housing via a pin that extends parallel to the first roller,
    a second roller extending parallel to the first roller, the second roller being positioned within the cavity, the second roller comprising a gripping portion and a ratchet portion, the gripping portion, the pawl and the ratchet portion being positioned outside of the cavity, the gripping portion having a maximum diameter that is greater than that of the ratchet portion, the ratchet portion comprising a plurality of angled teeth circumferentially disposed about the ratchet portion, the teeth engaging the projection such that the second roller may be rotated in a first direction and is prevented from being rotated in an opposite second direction, wherein the top wall has a maximum length defined by a distance from a front edge of the top wall to a back edge of the top wall, the front edge being positioned between the rollers,
    a strip extending through the openings, the strip having a first end that is wound about the first roller, a second end that is wound about the second roller and an intermediate portion that directly engages an outer surface of the top wall that is opposite the inner surface of the top wall, and
    a plurality of instrument covers positioned on one side of the strip;
  at least one box of gloves; and
  at least one stethoscope.

* * * * *